US006277129B1

(12) United States Patent
Poran

(10) Patent No.: US 6,277,129 B1
(45) Date of Patent: Aug. 21, 2001

(54) DUAL ENDED HAIR REMOVER

(75) Inventor: Yehuda Poran, Golan Heights (IL)

(73) Assignee: Epilady 2000, L.L.C., Hatzor Haglilit (IL)

( * ) Notice: Subject to any disclaimer, the term of this patent is extended or adjusted under 35 U.S.C. 154(b) by 0 days.

(21) Appl. No.: 09/598,498

(22) Filed: Jun. 22, 2000

(51) Int. Cl.[7] .................................................... A61B 17/50
(52) U.S. Cl. ........................................... 606/133; 30/34.05
(58) Field of Search .................................... 606/133, 131, 606/210, 211, 41–50; 30/34.05, 90, 45, 43.92, 43.91

(56) References Cited

U.S. PATENT DOCUMENTS 3,672,049 * 6/1972 Demci et al. ........................ 30/34.05
5,494,485 * 2/1996 Gabion et al. ........................ 606/133
5,611,804 * 3/1997 Heintke et al. ....................... 606/133
5,797,925 * 8/1998 Heintke ................................ 606/133
5,810,843 * 9/1998 Iwasaki et al. ....................... 606/133
6,083,233 * 7/2000 Kreutz et al. ......................... 606/133

* cited by examiner

*Primary Examiner*—Pedro Philogene
(74) *Attorney, Agent, or Firm*—Staas & Halsey LLP

(57) ABSTRACT

A dual ended hair remover which includes a casing having a motor, an epilating head for plucking hairs from the skin of a user attached to one end of the casing, a depilating head for cutting the hairs from the skin of the user attached to the other end of the casing, and a handle which covers one of the epilating and depilating heads while providing power to the other one of the epilating and depilating heads. The handle fits over one or the other end of the casing and provides power to the head which is not covered. The handle may also simultaneously provide power to the head which is covered. The handle protects the user and the unused head by covering the unused head and provides power to at least the head which is in use. Further, by incorporating the epilating and depilating heads on the casing at the same time and at opposite ends, ease of use is obtained. Still further, in the instances that only the head which is in use is being driven, power conservation is achieved.

41 Claims, 21 Drawing Sheets

DUAL ENDED HAIR REMOVER

BACKGROUND OF THE INVENTION

1. Field of the Invention

The present invention relates to a dual ended hair remover having depilating and epilating functions for removing hair from a user, and more particularly, to a dual ended hair remover having a casing with a depilating head fixed at one end thereof, an epilating head fixed at the opposite end thereof, and a handle which covers one of the depilating and epilating heads at a time while providing power to drive the other one of the depilating and epilating heads.

2. Description of the Related Art

Shaving devices are known which have multiple heads mounted thereon. The heads may either be permanently affixed to a casing having a motor or may be interchangeable. Such a device may even include a depilating head and an epilating head. A depilating head cuts hairs from the skin of a user, whereas an epilating head plucks (pulls) the hair from the skin of the user.

JP 4-348704, published Dec. 3, 1992 to Iwasaki, discloses a main body in which a motor is contained, an epilating block in which epilating means is contained and a trimmer. Both the epilating block and the trimmer are permanently affixed to one end of the main body, and they both operate simultaneously. The epilating block is at one side and the trimmer is at the other side of the same end, with the depilating block and the trimmer being in close proximity with each other. By being in close proximity with each other, there is a risk of injuring one's self through unintentional contact with the one of the depilating block and trimmer which is not intended to be used at a given time. In addition, as both the depilating block and trimmer operate simultaneously, although one is being used at a given time, unnecessary power is being used to drive the epilating/depilating appliance.

U.S. Pat. No. 3,672,049 issued Jun. 27, 1972 to Demci et al. discloses different operating heads as separate units for individual operation. The operating heads are both trimmers, which are interchangeable with each other at the same end of the casing 11. The two different types of trimmers are mounted one at a time to the casing 11. As a result, effort is required to interchange the two heads to perform the two different types of trimming and extra wearing of the components result from the repeated changing of the heads. Both heads are trimmers, and neither one performs the function of epilation. Also, as only one head is mounted at a time, the unmounted head may easily be lost by the user when not in use.

U.S. Pat. No. 5,611,804 issued Mar. 18, 1997 to Heintke et al. discloses a casing 2 which is adapted to receive a first attachment incorporating an epilating cylinder, or alternatively, a second attachment incorporating a long-hair trimmer. The first and second attachments are interchangeable with each other at a same end of the casing 2. Although Heintke et al. performs both the epilating and depilating functions, the appliance disclosed therein suffers from a number of the same drawbacks as are present in Demci et al. Namely, additional effort is required to replace the epilating head with the depilating head, and vice versa, when alternating between the epilating and depilating functions, and extra wearing of the components result from the repeated changing of the heads. Also, the unattached head may easily be lost by the user when not in use.

Other devices are known which have a shaving head and a long-hair trimmer at a same end of a casing, wherein either the shaver is in operation or both the shaver and the long-hair trimmer are in operation. In these devices, it is often easy to accidentally activate the long-hair trimmer, causing possible injury to the user when such operation is unaccounted for. Further, through the simultaneous operation of both the shaver and the long-hair trimmer, unnecessary power is required to drive both heads. Still further, such devices do not enable the epilation function to be performed.

SUMMARY OF THE INVENTION

Accordingly, it is an object of the present invention to provide a dual ended hair remover having both a depilating function and an epilating function.

It is another object of the present invention to provide a dual ended hair remover having a casing and a depilating head and an epilating head fixed at respective opposite ends of the casing.

It is a further object of the present invention to provide a dual ended hair remover having a casing, depilating and epilating heads fixed at respective opposite ends thereof, and a handle which alternately attaches to the opposite ends of the casing so as to cover one of the depilating and epilating heads while providing power to the other one of the depilating and epilating heads.

It is a further object of the present invention to provide a dual ended hair remover having a casing, depilating and epilating heads fixed at respective ends thereof, so as to lengthen the durability of the heads since there is no need to repeatedly detach and reattach the same.

It is still a further object of the present invention to provide a dual ended hair remover having a casing, depilating and epilating heads simultaneously fixed to the casing, and a handle which covers one of the depilating and epilating heads while providing power to the other one of the depilating and epilating heads.

It is still yet further another object of the present invention to provide a dual ended hair remover having a casing, depilating and epilating heads simultaneously fixed to the casing, and a handle which covers one of the depilating and epilating heads while providing power to the other one of the depilating and epilating heads, wherein the casing has a motor for driving the depilating and epilating heads, and a coupling unit to disengage the one of the depilating and epilating heads covered by the handle while engaging the motor and the one of the depilating and epilating heads which is not covered by the handle.

Additional objects and advantages of the invention will be set forth in part in the description which follows and, in part, will be obvious from the description, or may be learned by practice of the invention.

The above objects of the present invention are achieved by providing a dual ended hair remover to remove hairs from skin of a user, comprising a casing having first and second ends opposite each other, an epilating head mounted on the first end, to pluck the hairs from the skin of the user, and a depilating head mounted on the second end, to cut the hairs from the skin of the user.

The above and other objects are further achieved by providing a dual ended hair remover to remove hairs from skin of a user, comprising a casing having first and second ends opposite each other, an epilating head mounted on the casing, to pluck the hairs from the skin of the user, a depilating head mounted on the casing, to cut the hairs from the skin of the user, and a handle to alternately cover the epilating head and enable driving of the depilating head, and cover the depilating head and enable driving of the epilating head. The above and other objects are still further achieved by providing a dual ended hair remover to remove hairs from skin of a user, comprising a casing having first and second ends opposite each other, an epilating head mounted on the casing, to pluck the hairs from the skin of the user, a depilating head mounted on the casing, to cut the hairs from the skin of the user, and a handle to alternately cover the epilating head and enable driving of the depilating head without enabling driving of the epilating head, and cover the depilating head and enable driving of the epilating head without enabling driving of the depilating head.

BRIEF DESCRIPTION OF THE DRAWINGS

These and other objects and advantages of the invention will become apparent and more readily appreciated from the following description of the preferred embodiments, taken in conjunction with the accompanying drawings of which.

DESCRIPTION OF THE PREFERRED EMBODIMENTS

Figure 1A:
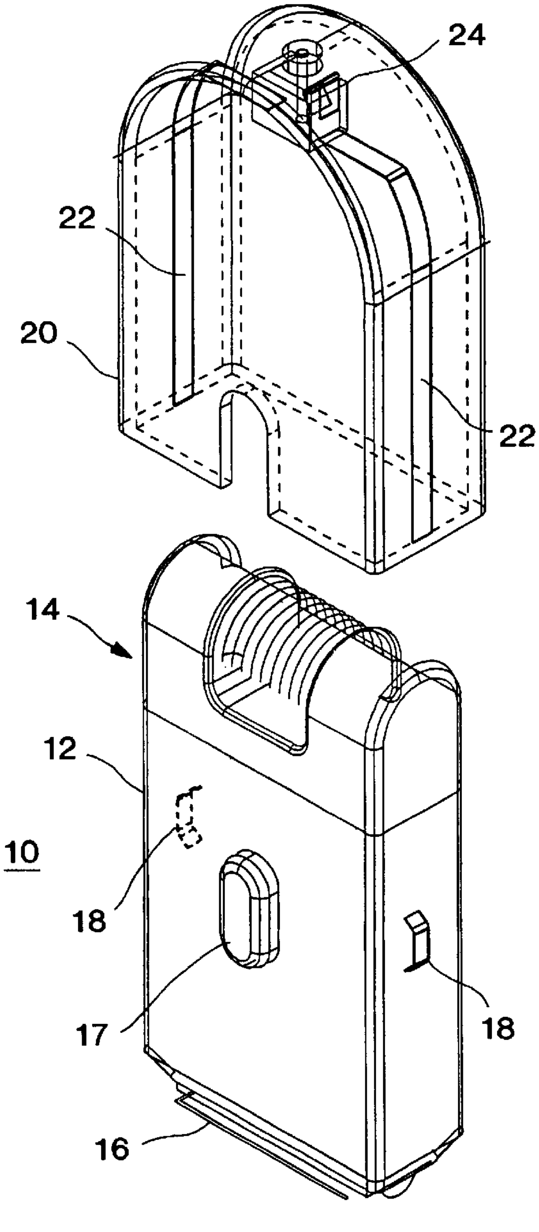
FIGS. 1A and 1B are perspective views of a dual ended hair remover having a handle being attached to one end of a casing so as to cover an epilating unit and attached to the other end of the casing so as to cover a depilating unit, respectively.

Reference will now made in detail to the present preferred embodiments of the present invention, examples of which are illustrated in the accompanying drawings, wherein like reference numerals refer to the like elements throughout.

Figure 1B:
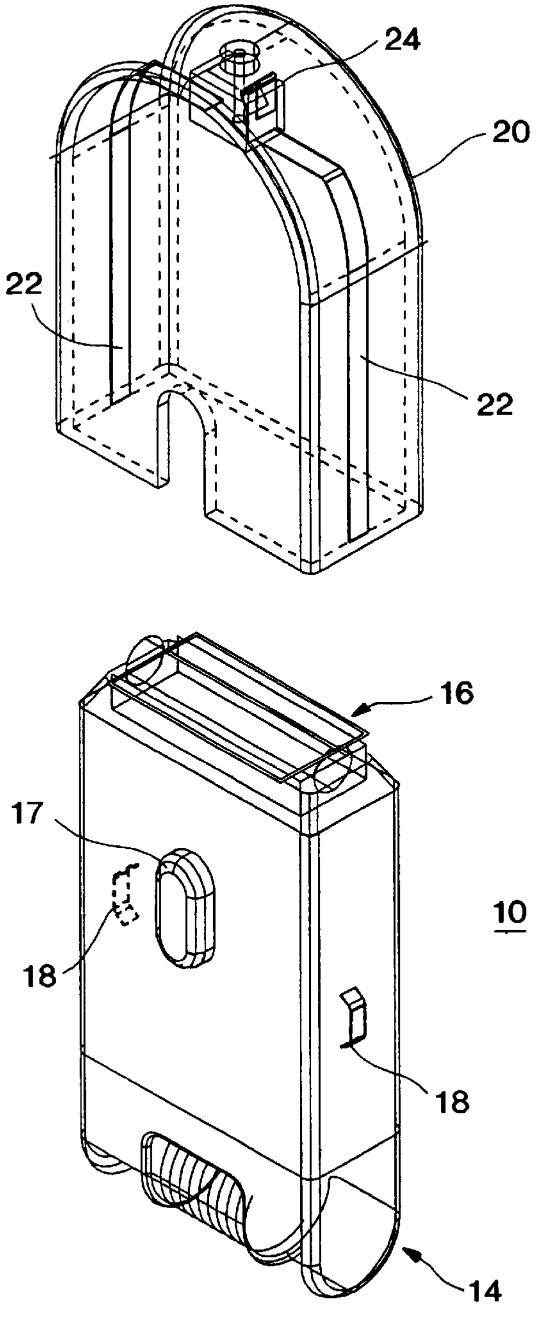

FIGS. 1A and 1B are perspective views of a dual ended hair remover in accordance with the first embodiment of the present invention. The dual ended hair remover 10 has a casing 12, an epilating head attached to one (a first) end of the casing and a depilating head (shaving unit) attached to the other (second) end of the casing 12. A pair of contacts 18 are exposed at respective opposite sides of the casing 12, in between the epilating head 14 and the depilating head 16. An on/off switch 17 extends from a middle of one of the surfaces of the casing 12 to control power to the epilating head 14 and the depilating head 16.

A handle 20 fits over either of the ends of the casing 12, selectively covering the epilating head 14 and the depilating head 16. A pair of terminals 22 are thin strips of metal extending in opposite directions from a power receptacle 24. The terminals 22 run along opposite sides of inner walls of the handle 20.

FIG. 1A shows the handle 20 about to be placed over (attached to) the first end of the casing 12 so as to cover the epilating head 14, and FIG. 1B shows the handle 20 about to be placed over (attached to) the other end of the casing 20 so as to cover the depilating head 16.

Regardless of whether the handle is placed over the first end or the second end of the casing 12, the terminals 22 respectively come into contact with the contacts 18 to provide electrical power to the contacts 18.

Figure 2A:
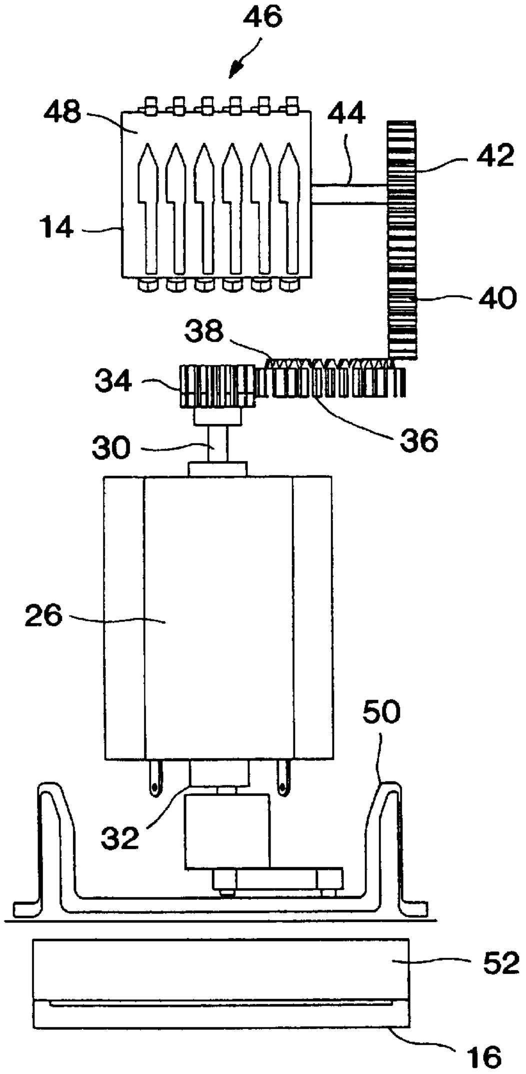
FIGS. 2A and 2B show a plan view and a perspective view of an internal mechanical configuration of the casing according to the first embodiment.
Figure 2B:
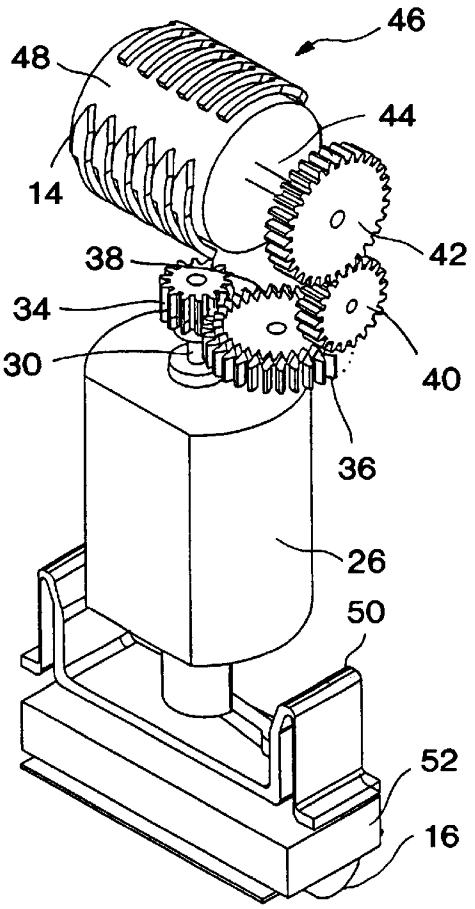

FIGS. 2A and 2B respectively show a plan view and a perspective view of the interior mechanical configuration region of the casing 12. A motor 26 is positioned near a center of the interior of the casing 12. First and second axles 30, 32 extend from opposite sides of the motor 26, the first axle 30 having an axis pointing toward the epilating head 14 and the second axle 32 having an axis of rotation directed toward the depilating head 16. When the handle 20 is placed over the epilating head 14 or the depilating head 16, the terminals 22 respectively come into contact with the contacts 18, thereby providing power to the contacts 18. The contacts 18 provide power to the motor 26 (see description of the electrical circuitry below), thereby causing the first and second axles 30, 32 to rotate.

A rotary gear 34 is affixed to the end of the axle 30 and is concentric thereto. A rotary gear 36 is permanently engaged with the rotary gear 34, has an axis of rotation parallel to that of the rotary gear 34, and has teeth 38 extending from the surface of the rotary gear 36 facing away from the motor 26. A rotary gear 40 is positioned at a right angle to the rotary gears 34 and 36, and permanently engages the teeth 38 of the rotary gear 36. A rotary gear 42 is affixed to an end of an axle 44 of the epilating head 14. Grippers 46 are formed at the periphery of an epilating cylinder 48 of the epilating head 14.

When the first axle 30 is driven by the motor 26, the rotary gear 34 is rotated, thereby rotating the rotary gear 36 and the teeth 38. The rotation of the teeth 38 causes the rotary gear 40 to rotate at a 90° angle relative to the rotary gear 36, thereby causing the rotary gear 42 to rotate. The rotation of the rotary gear 42 causes the axle 44 of the epilating cylinder 48 to rotate, thereby causing the grippers 46 to open and close, so as to pluck hairs from the skin of a user.

The motor 26 simultaneously drives the second axle 32, thereby causing a shaving element 50 to reciprocate back and forth relative to a fixed element 52. The reciprocation of the shaving element 50 relative to the fixed element 52 causes hair extending from the surface of the skin of the user between the shaving element 50 and the fixed element 52 to be cut.

Figure 3A:
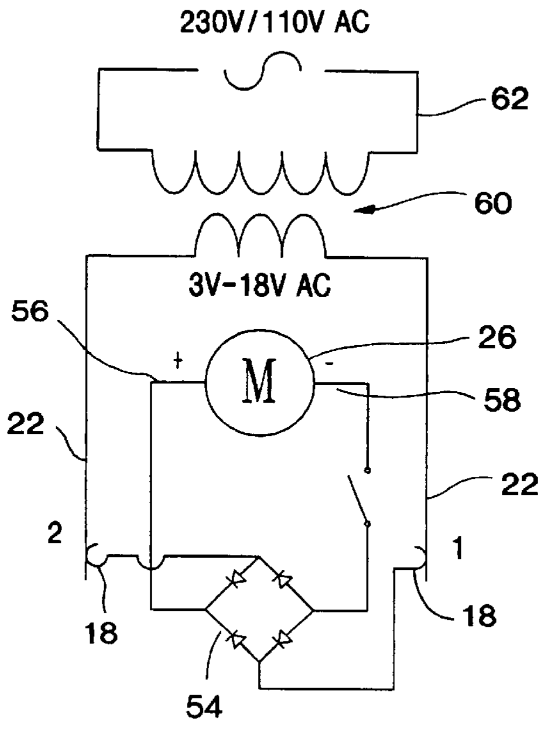
FIGS. 3A and 3B show electrical circuitry of the dual ended hair remover when the handle is attached to one end and the other end of the casing, respectively, according to the first embodiment of the present invention.
Figure 3B:
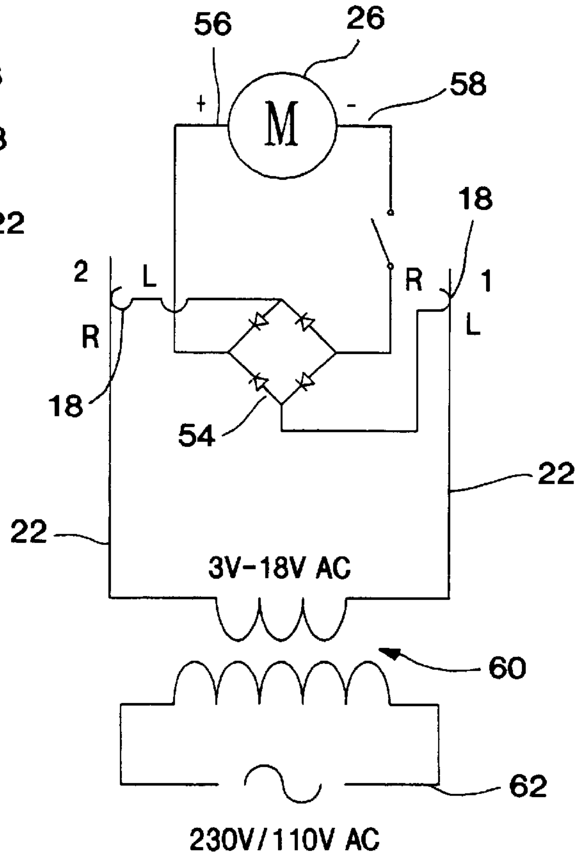

FIGS. 3A and 3B show a first situation wherein the handle 20 covers the epilating head 14, and a second situation wherein the handle 20 covers the depilating head 16, respectively. The contacts 18 are connected to two opposite points of a regulator (a wheatstone bridge) 54 and positive and negative poles 56, 58 of the motor 26 are connected to other opposite points of the regulator 54. A transformer 60 which is part of an external adapter (not shown) converts a 230V-110VAC from a wall socket 62 to 3V-18VAC which is transmitted through the power receptacle 24 to the terminals 22. When the handle 20 is placed over the first end to cover the epilating head 14 or the second end to cover the depilating head 16, power is supplied through the terminals 22 to the contacts 18, and subsequently to the motor 26 through the regulator 54 and the positive and negative poles 56, 58 of the motor 26.

As a result of this two-contact AC system, the electrical system forms an adapter which converts AC current to DC current inside the casing 12, so that there is no importance placed on the polarity of the contacts 18.

Figure 4A:
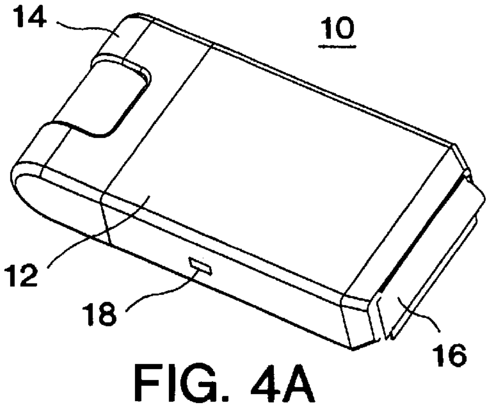
FIGS. 4A through 4D show various views of contacts exposed externally from the casing and terminals of the handle which contact the contacts of the casing according to the first embodiment of the present invention.
Figure 4B:
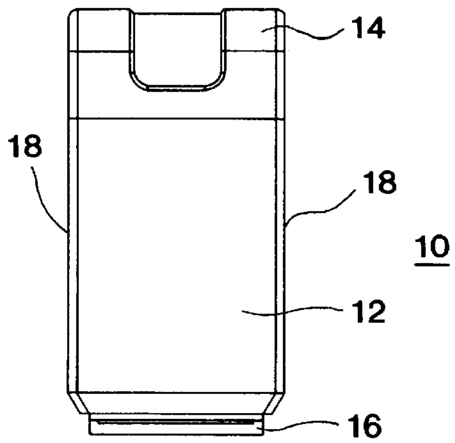
Figure 4C:
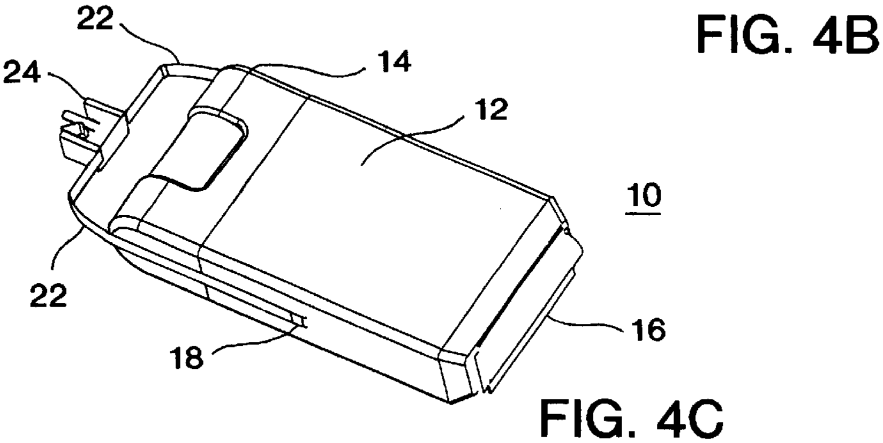
Figure 4D:
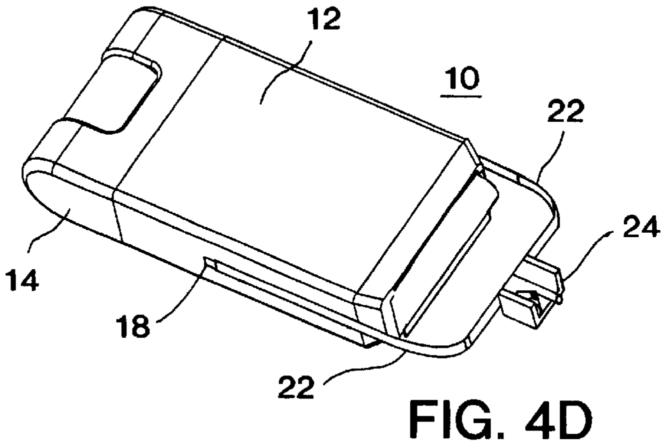

FIGS. 4A and 4B show a perspective view and a plan view of the dual ended hair remover 10 having the two-contact AC system, respectively, shown in FIGS. 1A through 3B. FIG. 4C shows the electrical contacts 22 respectively in contact with the contacts 18 when the handle 20 (the external portion of the handle 20 not being shown herein) is placed over the first end of the casing 12 to cover the epilating head 14. FIG. 4D shows the terminals 22 in contact with the contacts 18, respectively, when the handle 20 (the external portion of the handle 20 not being shown herein) is attached over the second end of the casing 12 to cover the depilating head 16.

Figure 5A:
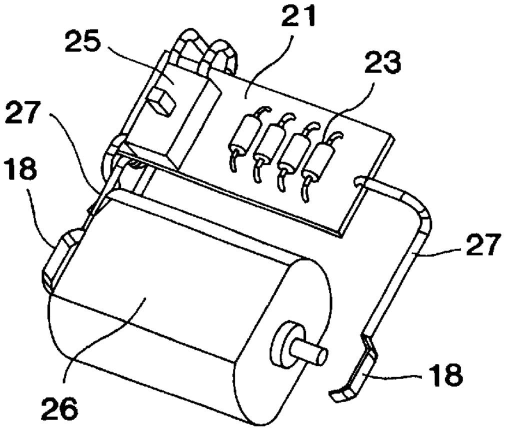
FIGS. 5A through 5D are various views of the internal electrical system according to the first embodiment of the present invention using a two-contact AC system.
Figure 5C:
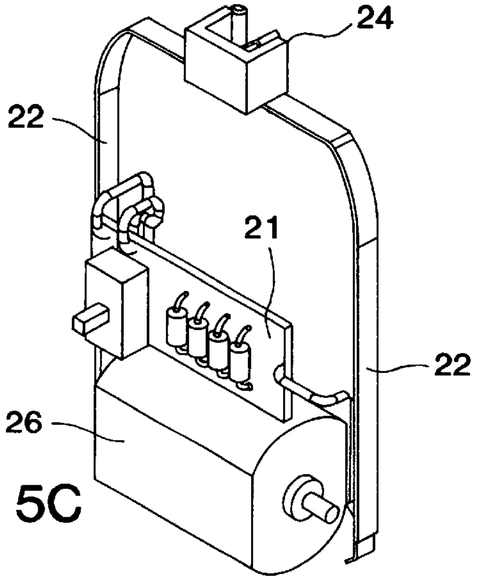
Figure 5B:
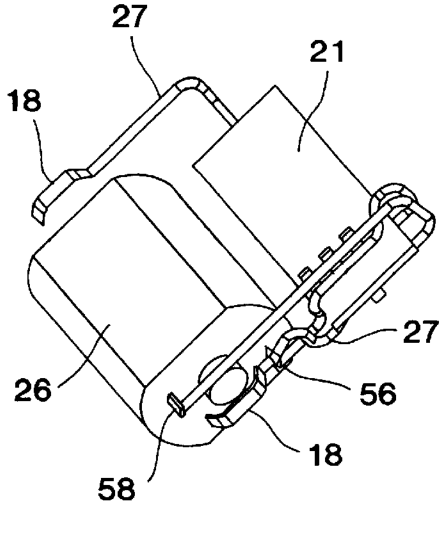
Figure 5D:
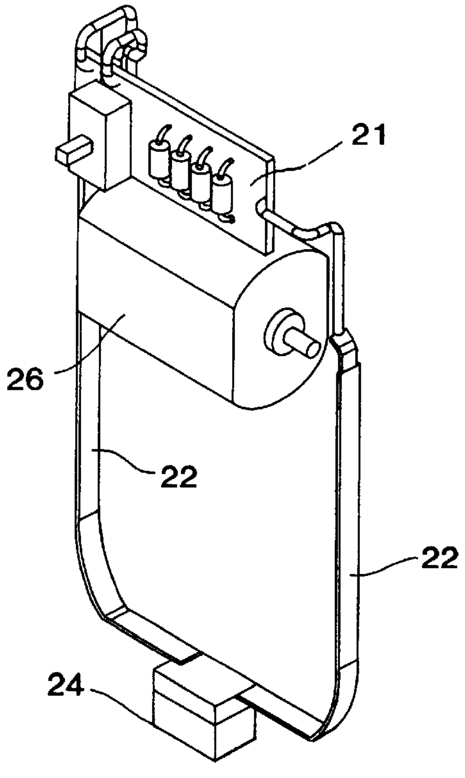

FIGS. 5A through 5D show various views of the internal electrical circuitry for the two contact AC power system shown in FIGS. 3A through 4D. FIG. 5A shows a front perspective view of the electrical circuitry, FIG. 5B shows a back perspective view of the electrical circuitry, FIG. 5C shows the terminals 22 of the handle 20 (not shown in this drawing) contacting the respective contacts 18 when the handle 20 is mounted at one end of the casing 12 to cover the epilating head 14, and FIG. 5D shows the terminals 22 in contact with the respective contacts 18 when the handle 20 (not shown in this drawing) is mounted on the other end of the casing 12 to cover the depilating head 16.

A printed circuit board (PCB) 21 has two diodes 23 and a switch 25 mounted thereon. The PCB 21 receives AC current from the contacts 18 which are supplied from the terminals 22 (see FIGS. 5C and 5D).

FIG. 5B shows wires 27 that conduct the AC current from the contacts 18 from both sides to the rectifier 54 shown in FIGS. 3A and 3B, and then the DC direct current is supplied to the positive and negative leads (motor poles) 56, 58 of the motor 26.

A variety of other mechanical configurations and electrical circuitries may be adapted for use in the present invention, some of which are explained below.

Figure 6A:
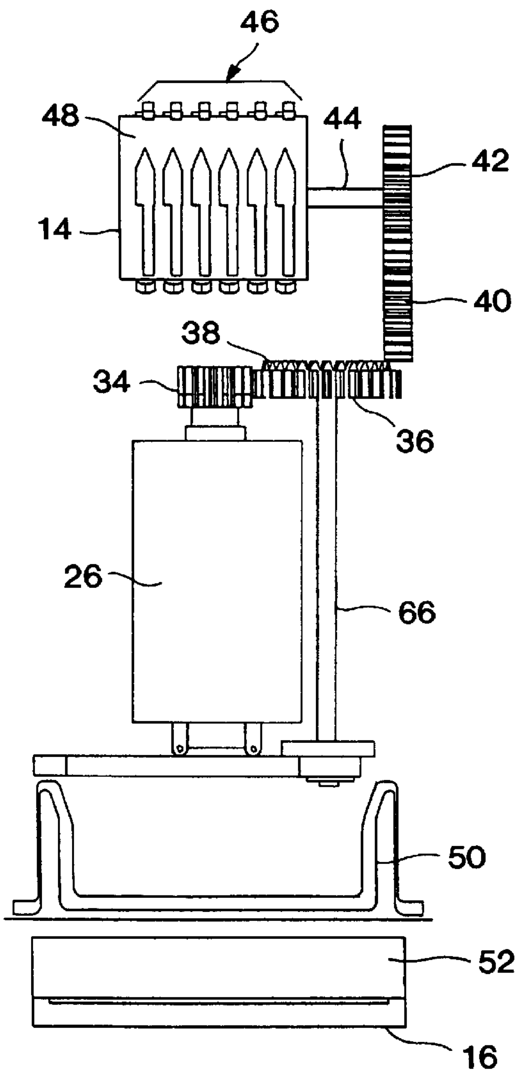
FIGS. 6A and 6B show a plan view and a perspective view of an internal mechanical configuration of the casing, respectively, according to a second embodiment of the present invention.
Figure 6B:
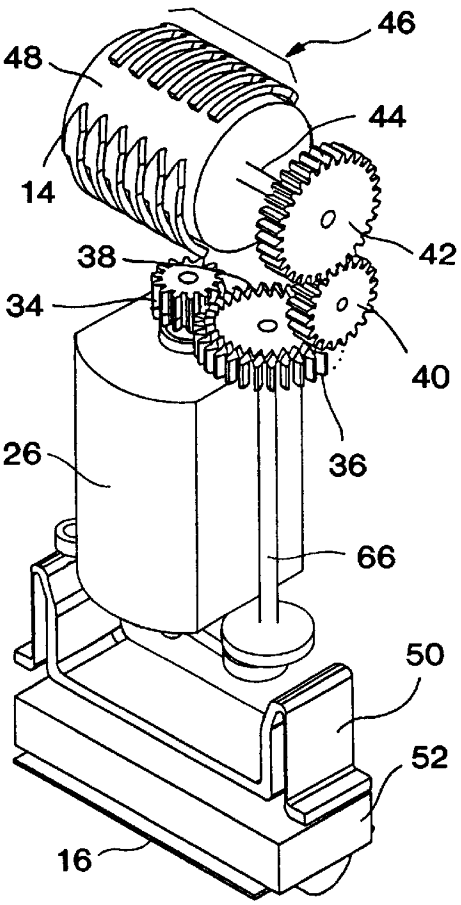

FIGS. 6A and 6B show a plan view and a perspective view of the internal mechanical configuration of the casing 12 according to a second embodiment of the present invention. The mechanical elements and operation of the mechanical elements are substantially the same as the internal mechanical elements shown in FIGS. 2A and 2B with the following exceptions.

Instead of the second axle 32 extending from the opposite side of the motor 26 to that of the first axle 30 to reciprocatingly drive the shaving element 50, a second axle 66 is attached to the rotary gear 36 so as to extend parallel to the first axle 30 alongside the motor 26 and past the motor 26. The end of the second axle 66 opposite the rotary gear 36 is attached to the shaving element 50. When the motor 26 is driven, the first axle 30 rotates, thereby rotating the rotary gear 36. As a result of rotation of the rotary gear 34, the rotary gear 36 rotates, thereby rotating the second axle 66, to cause the reciprocating movement of the shaving element 50 relative to the fixed element 16. As a result, hair positioned between the shaving element 50 and the fixed element 52 is cut, as in the first embodiment. The epilating cylinder 48 is driven simultaneously with the shaving element 50, with either the epilating head 14 or the depilating head 16 being covered by the handle 20.

Figure 7A:
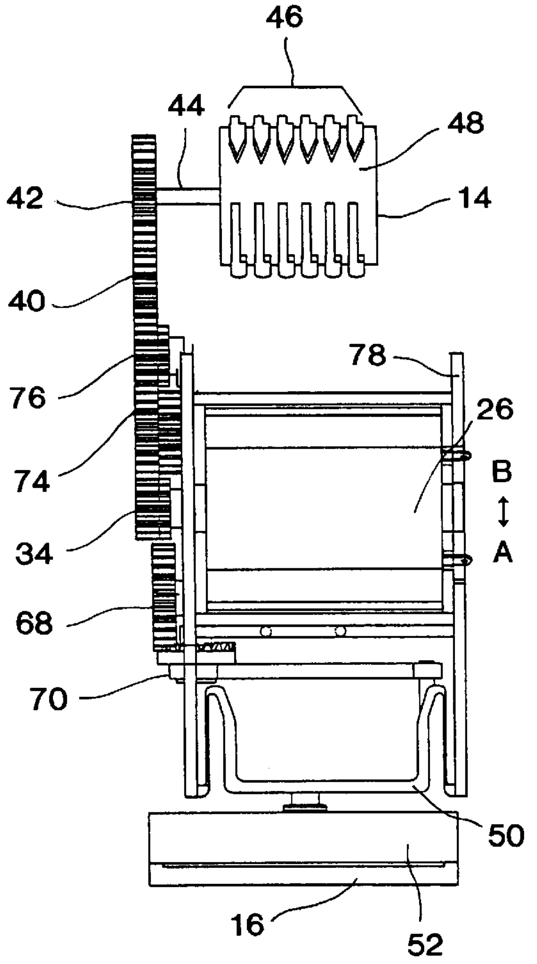
FIGS. 7A and 7B show a plan view and a perspective view of an internal mechanical configuration of the casing, respectively, according to a third embodiment of the present invention.
Figure 7B:
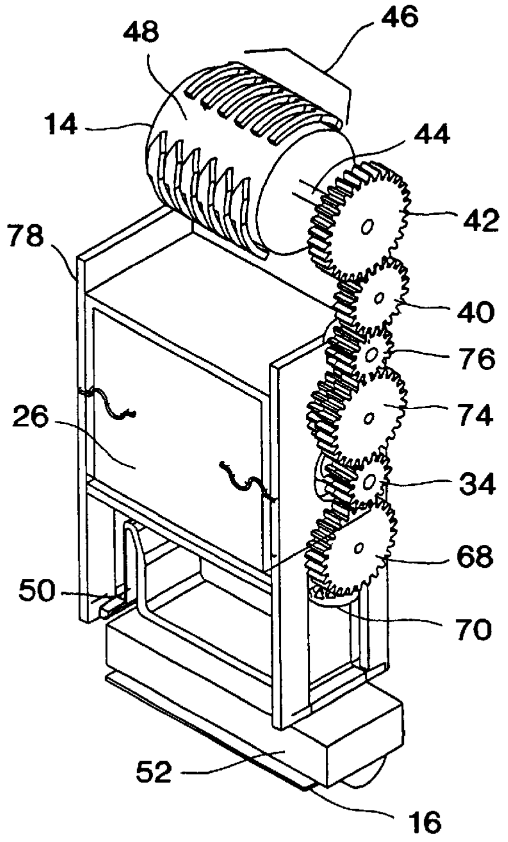

FIGS. 7A and 7B show a plan view and a perspective view of the internal mechanical portion of the casing 12 for driving the epilating head 14 and the depilating head 16 according to a third embodiment of the present invention. In this third embodiment, instead of the motor extending in a lengthwise direction of the casing 12 in a direction from the epilating head 14 to the depilating head 16, the motor is rotated 90° from that of the first and second embodiments shown in FIGS. 1A through 5B. In this third embodiment, the motor 26 extends in a direction from one side of the casing 12 to the other side, and not in a direction from one end to the other. A bracket 78 is fixed within the casing 12. The motor 26 is mounted in the bracket 78 and is movable between a position A and a position B. The mounting of the handle 20 on the epilating head 14 or the depilating head 16 or a switch in the interior of the handle 12 based upon the mounting of the handle 12 on the epilating head 14 or the depilating head 16 may be used to move the motor between the positions A and B. The first axle 30 extends from one side of the motor 26 and is rotated in conjunction with the driving of the motor 26. The rotary gear 34 is coaxial with and placed at the end of the first axle 30.

A rotary gear 38 has an axis of rotation parallel to the axis of rotation of the rotary gear 34 and is positioned at a right angle relative to a rotary gear 70. A rotary gear 70 has teeth 72 extending from a surface thereof to permanently engage with the rotary gear 68. The rotary gear 70 is connected to the shaving element 50. A rotary gear 74 has an axis of rotation parallel to the axis of rotation of rotary gear 34, and is permanently engaged with a rotary gear 76. The rotary gear 76 is permanently engaged with the rotary gear 40.

In the position A (when the handle 20 is mounted over the epilating head 14), the rotary gear 34 attached to the first axle 30 engages with the rotary gear 68, and is disengaged from the rotary gear 74. The rotation of the rotary gear 34 causes the rotary gears 68 to rotate, thereby causing the rotary gear 70 to rotate through the interaction of the teeth 72 with the rotary gear 68. The rotation of the rotary gear 70 causes the shaving element 50 to move in a reciprocating motion relative to the fixed element 52 of the depilation head 16.

When the motor 26 is in the position B (when the handle 20 is mounted over the depilating head 16), the rotary gear 36 engages the rotary gear 74, and is disengaged from the rotary gear 68. The rotation of the rotary gear 34 causes the rotation of the rotary gears 74, 76, 40, and 42, thereby causing rotation of the epilating cylinder 48. As a result, the grippers 46 open and close to pull the hair, positioned between the grippers, from the skin of the user.

The two contact system shown in FIGS. 1A, 1B and 3A through 4B may be used to power the motor 26.

In the third embodiment, because the motor 26 is movable between the positions A and B, it is possible to selectively drive the epilating head 14 and the depilating head 16, only when necessary. Therefore, if the epilating head 14 is covered by the handle 20, only the depilating head 16 need be driven. If the depilating head 16 is covered by the handle 20, only the epilating head 14 need be driven. Such a configuration saves power by not simultaneously driving both the epilating head 14 and the depilating head 16 while only one head is being used while the other one is covered.

Figure 8A:
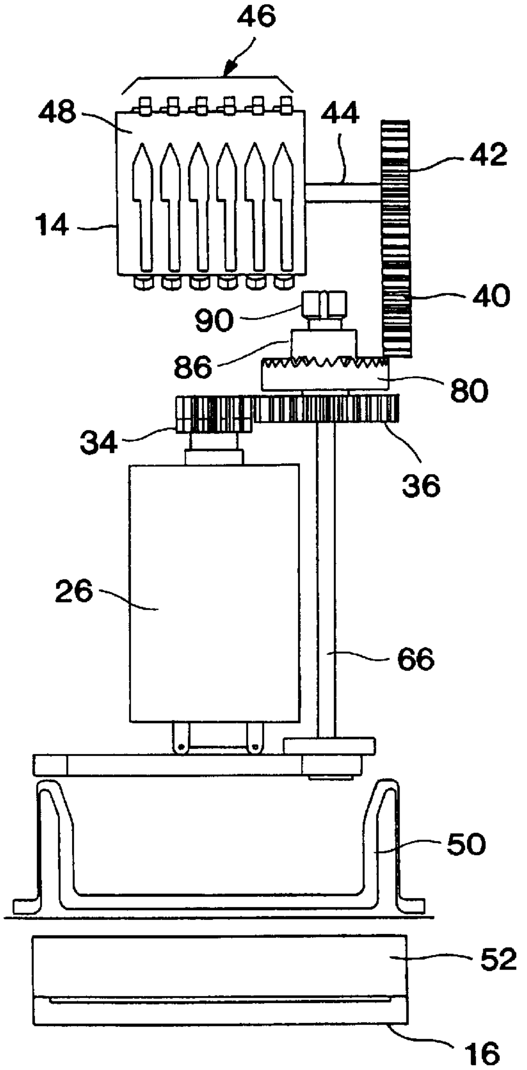
FIGS. 8A and 8B show a plan view and a perspective view of an internal mechanical configuration of the casing, respectively, according to a fourth embodiment of the present invention.
Figure 8B:
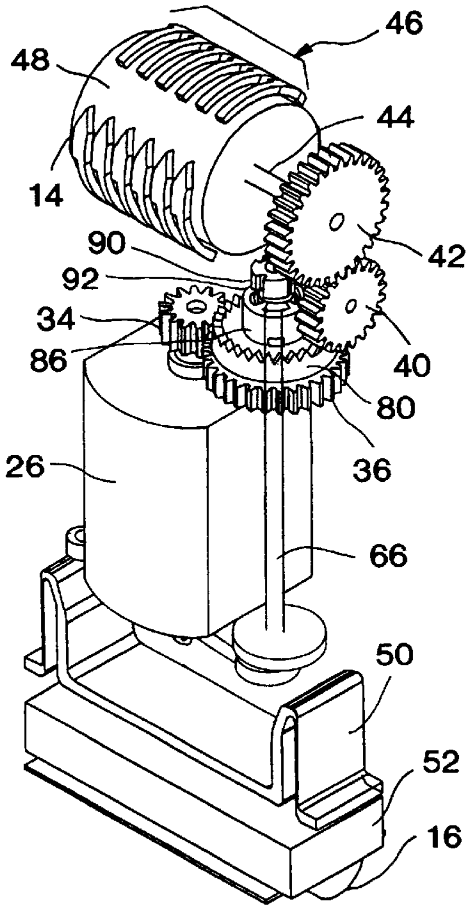
Figure 9A:
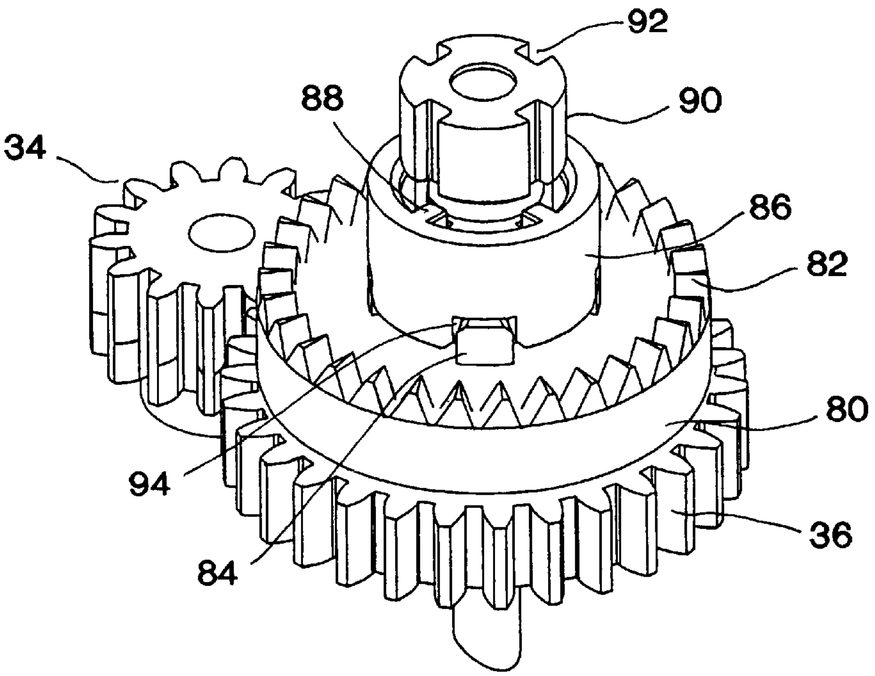
FIGS. 9A and 9B show a coupling unit having a coupler at first and second positions, to selectively drive an epilating head and a depilating head, respectively, according to the fourth embodiment of the present invention.
Figure 9B:
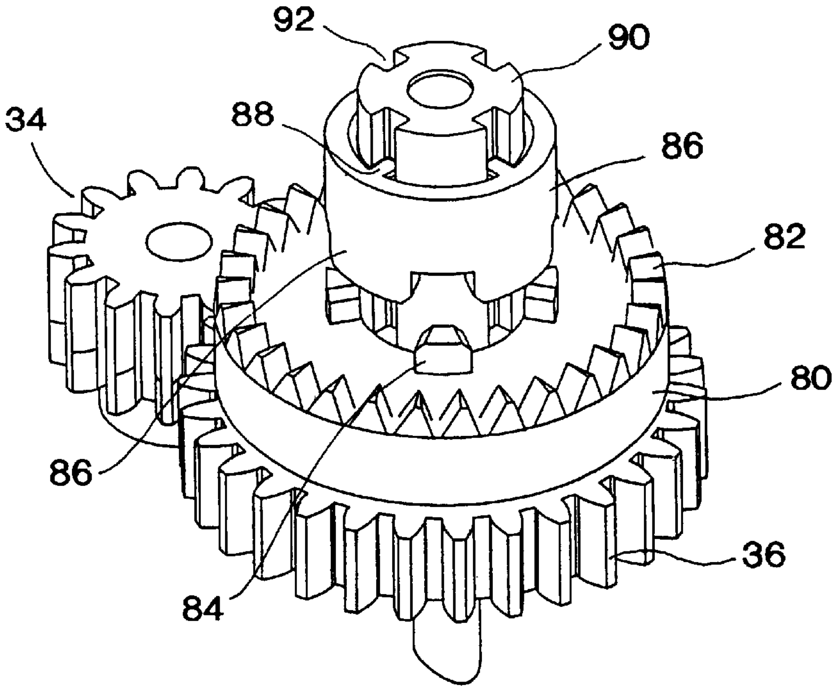
Figure 10:
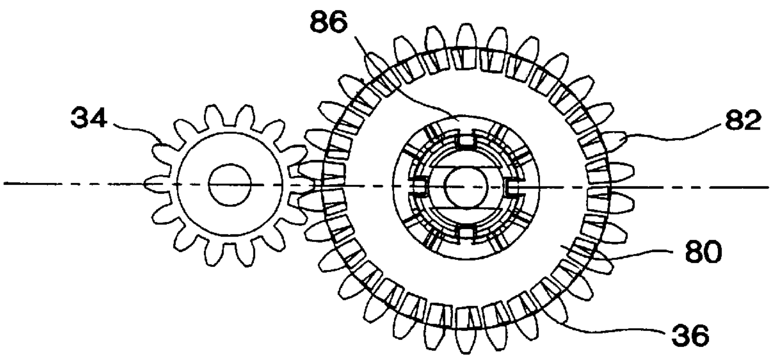
FIG. 10 shows a plan view of rotary gears and the coupler according to the fourth embodiment of the present invention.
Figure 11A:
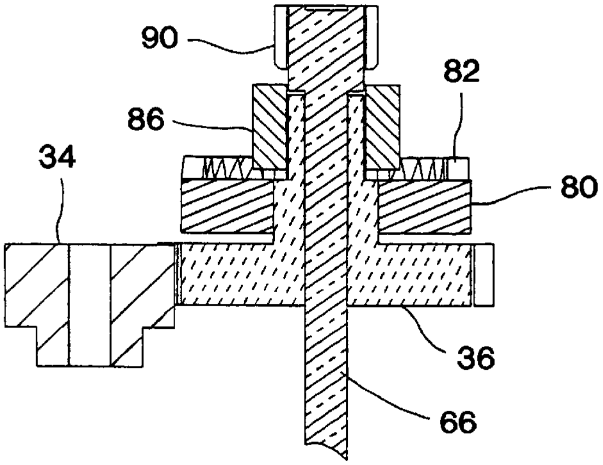
FIGS. 11A and 11B show a cross-sectional view of the coupler at the first and second positions, respectively, according to the fourth embodiment of the present invention.
Figure 11B:
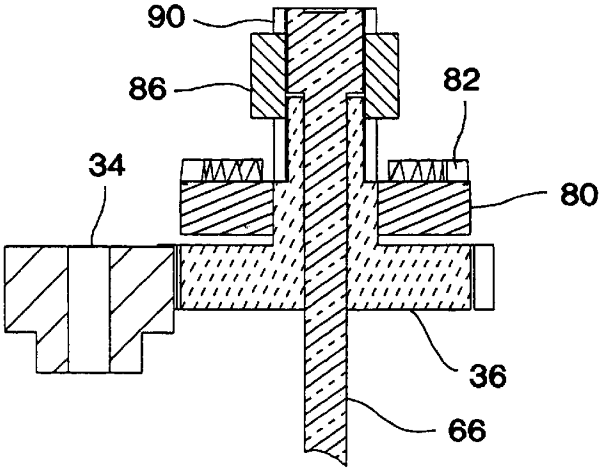
Figure 12:
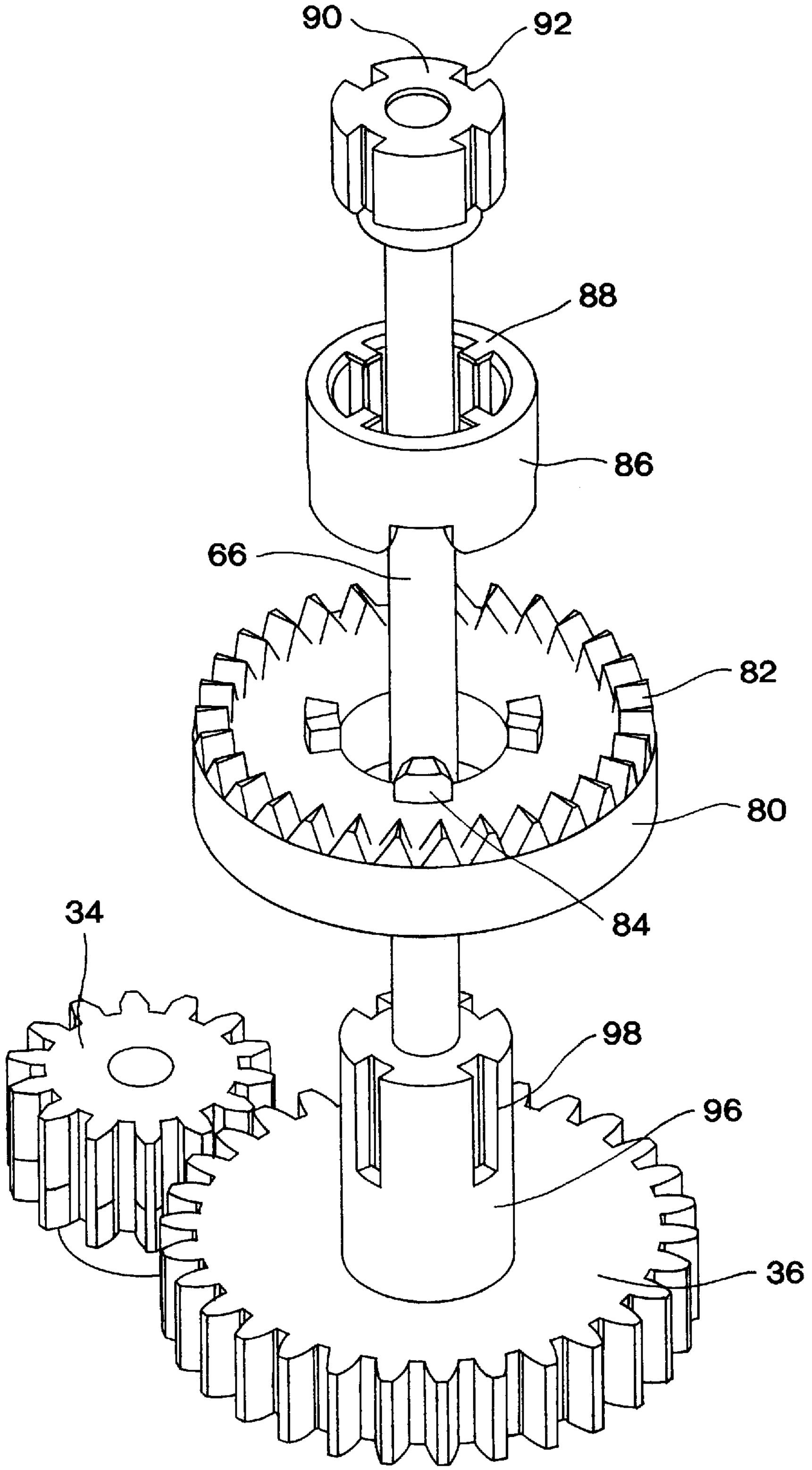
FIG. 12 is an exploded view of the coupler according to the fourth embodiment of the present invention.

FIGS. 8A and 8B show a plan view and a perspective view of the internal mechanical configuration and operation of the casing 12, respectively, according to a fourth embodiment of the present invention. Many of the mechanical parts are very similar to those shown in FIGS. 6A and 6B, except there are distinctions to enable selective driving of the epilation head 14 and the depilation head 16 as in the third embodiment shown in FIGS. 7A and 7B. Like the second embodiment shown in FIGS. 6A and 6B, the rotary gear 34 is currently engaged with the rotary gear 36. However, instead of the rotary gear 36 having teeth extending from a surface thereof, another rotary gear 80 is adjacent to the rotary gear 36, but may or may not rotate based upon the rotation of the rotary gear 36. The rotary gear 80 has teeth extending from a surface thereof in a direction toward the epilating head 14. Further, the rotary gear 80 has a hole in the middle and protrusions 84 at a periphery of the hole and extending from the same surface as the teeth at 90° intervals. The second axle 66, unlike in the second embodiment shown in FIGS. 6A and 6B, extends beyond the rotary gear 36 and through the hole of the rotary gear 80. A spline 90 is fixedly formed at the end of the axle 66 and has slots 92 formed at 90° intervals. A coupler 86 having protrusions 88 is selectively moved linearly to either engage the protrusions 84 or the slots 92 of the spline 90. FIGS. 9A and 9B show a more detailed perspective view of the coupler 86 engaging the protrusions 84 of the rotary gear 80 and the slots 92 of the spline 90, respectively. FIG. 10 shows a plan view of the rotary gear 34 engaged with the rotary gear 36, and the rotary gear 80 and the coupler 86 positioned above the rotary gear 36. FIGS. 11A and 11B are cross-sectional views of the coupling unit shown in FIGS. 9A and 9B, respectively. FIG. 12 shows an exploded view of the coupling unit shown in FIGS. 9A through 11B.

In FIGS. 9A and 11A, the coupler has been moved into a first position so that recesses 94 formed therein to correspond with the protrusions 84 of the rotary gear 80 are engaged by the protrusions 84. A description of the how the coupling moves between the first and second positions will be described later in the specification.

As shown in FIG. 12, the rotary gear 36 has a thickened region 96 extending therefrom and through the hole of the rotary gear 80. The thickened region 96 is coaxial with the second axle 66, and has slots 98 formed at 90° relative to each other and extending along the lengthwise direction of the second axle 66. The protrusions 88 of the coupler 86 are slidable within the slots 98 of the thickened region 96, and as the rotary gear 36 and the thickened region 96 rotate, the coupler 86 is rotated through the interaction of the protrusions 88 and the slots 98.

A description of the mechanical operation according to the fourth embodiment when the coupler 86 is in the first position will now be described. As the motor 26 is driven, the axle 30 rotates the rotary gear 34 so that the rotary gear 36 is rotated. The rotation of the rotary gear 36 causes the thickened region 96 to rotate so that the coupler 86 rotates through the interaction between the slots 98 and the protrusions 88. The interaction between the engagement of the protrusions 84 of the rotary gear 80 and the recesses 94 of the coupler 86 cause the rotary gear 80 to rotate. Because the teeth 82 of the rotary gear 80 are permanently engaged with the rotary gear 40, the rotary gear 40 is rotated, thereby rotating the rotary gear 42. As a result, the axle 44 is rotated, to thereby rotate the epilating cylinder 48, which in turn causes the grippers 46 to rotate and open and close. Based upon the rotation and opening and closing of the grippers 46, the hairs from the skin of the user are plucked, to accomplish the epilation function. FIGS. 9B and 11B show when the coupler 86 is in the second position. At this time, the recesses 94 disengage from the protrusions 84 of the rotary gear 80, and the protrusions 88 engage with the slots 92 of the spline 90. When the coupler 86 is in this second position, the protrusions 88, which extend through the height of the coupler 86 are within both the corresponding slots 98 and the corresponding slots 92.

When the motor 26 is driven, the first axle 30 rotates the rotary gear 34, thereby rotating the rotary gear 36. The thickened region 96 rotates in conjunction with the rotary gear 36, thereby causing the rotation of the coupler 86 through the interaction of the engagement of the protrusions 88 within the corresponding slots 98. Simultaneously, the protrusions 88 are at least partially engaged in the corresponding slots 92 of the spline 90, thereby rotating the second axle 66. The rotation of the second axle 66 causes the shaving element 50 to move in the reciprocating motion relative to the fixed element 52, thereby cutting the hairs from the skin of the user which are positioned between the sharing element 50 and the fixed element 52.

Figure 13:
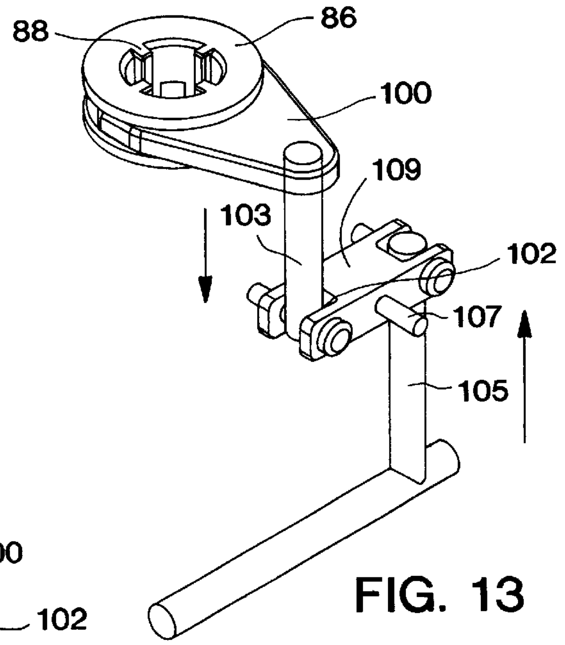
FIG. 13 shows a coupling mechanism to move the coupler between the first and second positions according to the fourth embodiment of the present invention.
Figure 14:
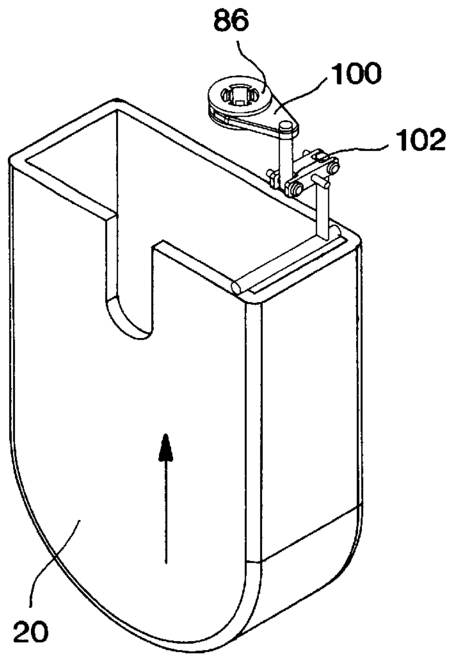
FIG. 14 shows the coupling mechanism along with the coupler and attached to the handle according to the fourth embodiment of the present invention.
Figure 15:
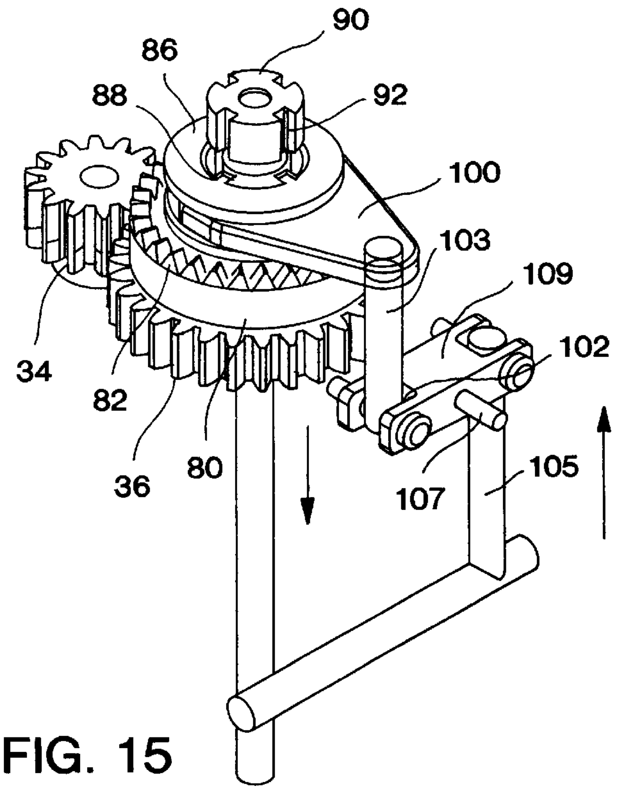
FIG. 15 is an in-depth view of the coupler and the coupling mechanism according to the fourth embodiment of the present invention.

FIGS. 13 through 15 show a coupling mechanism for moving the coupler 86 between the first and second positions. FIG. 13 shows a fork 100 which is connected at one end to the coupler 86 so that a portion of the fork 100 goes around part of the periphery of the coupler 86. The other end of the fork 100 is fixed to a lever mechanism 102 which extends perpendicularly from the bottom surface (see FIG. 12) of the fork 100. The lever mechanism 102 includes an H-shaped bracket having a protrusion 107 fixed to an interior portion of the casing 12 so that the H-shaped bracket 109 is rotatable about an axis of the cylindrical protrusion 107. A cylindrical piece 103 is fixed in between one of the gaps of the H-shaped bracket 109 at one end and to the fork 100 at the other end thereof. A T-shaped arm 105 has one end fixed to the other gap in the H-shaped bracket 109. FIG. 14 shows the coupler 86, the fork 100 and the lever mechanism 102 (which are in the interior part of the casing 12) which are pushed in one direction by the handle 20 when the handle 20 is mounted on the casing 12. When the handle 20 is inserted over one end of the casing 12 to cover the epilating head 14, the T-shaped arm 105 is moved downward (in FIGS. 13 through 15), the H-shaped bracket 109 is rotated clockwise about the cylindrical protrusion 107 and the cylindrical piece 103 is pushed upward, thereby pushing the fork and coupler upward to the first position to engine the spline 90. When the handle 20 is removed from the casing 12 and inserted over the other end of the casing 12 to cover the depilation 16, the T-shaped arm 105 is moved upward, thereby causing the H-shaped bracket 109 to rotate counterclockwise about the cylindrical protrusion 107. As a result, the cylindrical piece 103 is pulled downward, thereby moving the fork 100 and the coupler 86 downward to the first position. Then, the protrusions 84 of the rotary gear 80 engage the recesses 94 of the coupler 86. A more detailed view of the interaction between the lever mechanism 102 and the fork 100 is shown in FIG. 15. The handle 20 contacts the lever mechanism 102 through a track in the casing 12. When the handle 20 is inserted over one end of the casing 12 to cover the epilating head 14, the lever mechanism 102 pushes against the fork 100 to move the coupler 86 to the second position. When the handle 20 is removed from the casing 12 and inserted over the other end of the casing 12 to cover the depilation head 16, the lever mechanism 102 pushes on the opposite side of the fork 100 to move the coupler 86. A more detailed view of the interaction between the lever mechanism 102 and the fork 100 is shown in FIG. 15.

Based upon the positioning of the handle 20, the lever mechanism 102 pushes or pulls the fork 100 to selectively move the coupler 86 to the first and second positions, thereby selectively driving the one of the epilating head 14 and the depilating head 16 which is positioned at the opposite end of the casing 12 from which the handle 20 is mounted. Therefore, when the handle 20 covers the epilating head 14, the depilating head 16 is driven by the coupler 86 being positioned at the second position, whereas when the handle 20 covers the depilating head 16, the epilating head 14 is driven by the movement by the coupler 86 to the first position.

Figure 16:
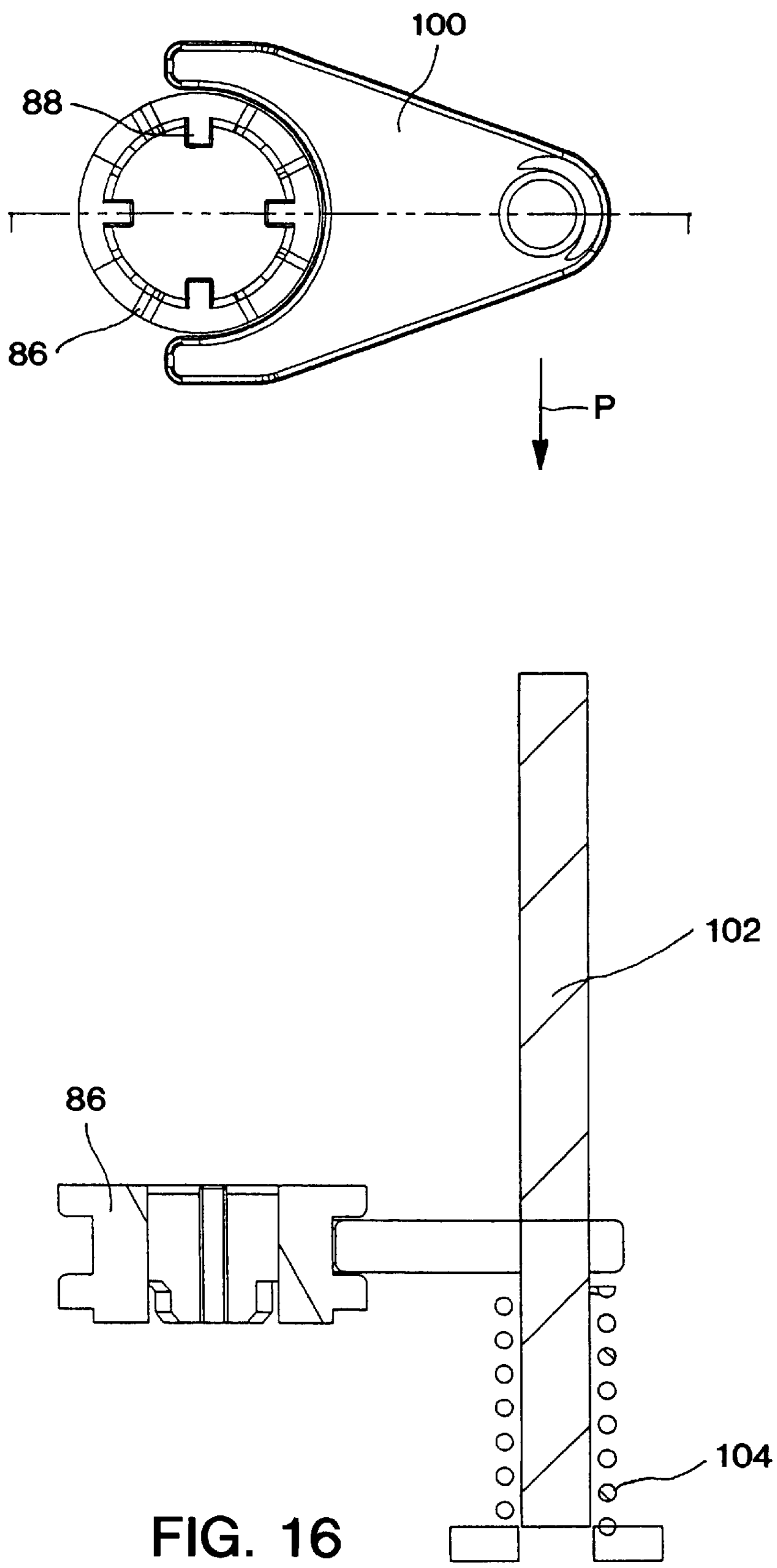
FIG. 16 shows a coupling mechanism for driving the coupler between the first and second positions in a second aspect according to the fourth embodiment of the present invention.

Another possible coupling mechanism for moving the coupler 86 between the first and second positions to alternately engage the epilating head 14 and the depilating head 16 is shown in FIG. 16 according to another aspect of the fourth embodiment of the present invention. A spring 104 biases the lever mechanism 102 so that the fork 100 is in either the first or second position, and as shown in the drawing, biases the lever mechanism 102 so that the fork 100 is in the second position so that the protrusions 88 engage the slots 92 of the spline 90. When the handle 20 is mounted on the depilating head 16, the handle 20 moves the lever mechanism 102 to push down on the fork 100, thereby moving the coupler 86 to the first position against the bias of the spring 104. As a result, the coupler 86 disengages from the spline 90 and the recesses 94 of the coupler 86 are engaged by the protrusions 84 of the rotary gear 80. When the handle 20 is removed from the depilating head 16, the coupler 86 is moved back to the second position through the bias of the spring 104.

Based upon the two aspects described above regarding the movement of the coupler 86 between the first and second positions, it is possible to alternately engage the epilating head 14 and the depilating head 16, so that only one head is operating at a given time. As are result, power is conserved, and wear and tear on the epilating and depilating heads 14, 16 are minimized.

Of course, one of ordinary skill in the art would recognize that there are any number of different ways to move the coupler 86 between the first and second positions to selectively engage the splines 90 and the protrusions 84 of the rotary gear 80.

Figure 17A:
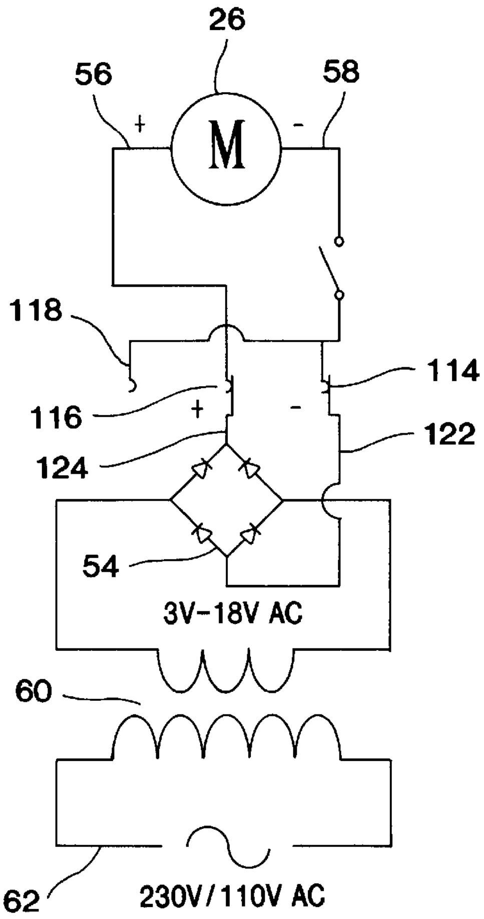
FIGS. 17A and 17B show the internal electrical circuiting of a casing based upon whether a handle is attached to a first end or a second end of the casing, respectively, according to a fifth embodiment of the present invention.

FIGS. 17A through 19C show another electrical system for supplying power to the motor 26 using a three-contact AC system according to a fifth embodiment of the present invention. In the three-contact AC system, the transfer of current is performed by an adapter within a casing 112, wherein there are three contacts instead of two. FIGS. 17A and 17B show the internal schematic drawings of the power electrical system of the dual ended hair remover when the handle 20 is attached to one end of the casing 112 which covers the epilating head 14 and when the handle is connected to the other end of the casing 112 to cover the depilating head 16. As shown in FIGS. 18A through 18C, the casing 112 differs from the casing 12 in that there are three contacts 114, 116 and 118 which are exposed externally from the casing 112. The handle 20, instead of having terminals 22 extending along the inner peripheries of opposite sides of the handle 20, has terminals 122, 124 extending along an inner surface of the back of the handle 20.

The central contact 116 has a positive polarity, while the outside contacts 114, 118 have a negative polarity and are connected together. The central contact 116 is connected to one end of the rectifier 54, whereas the outside contacts 114 and 118 are connected to the other end of the rectifier 54.

Figure 17B:
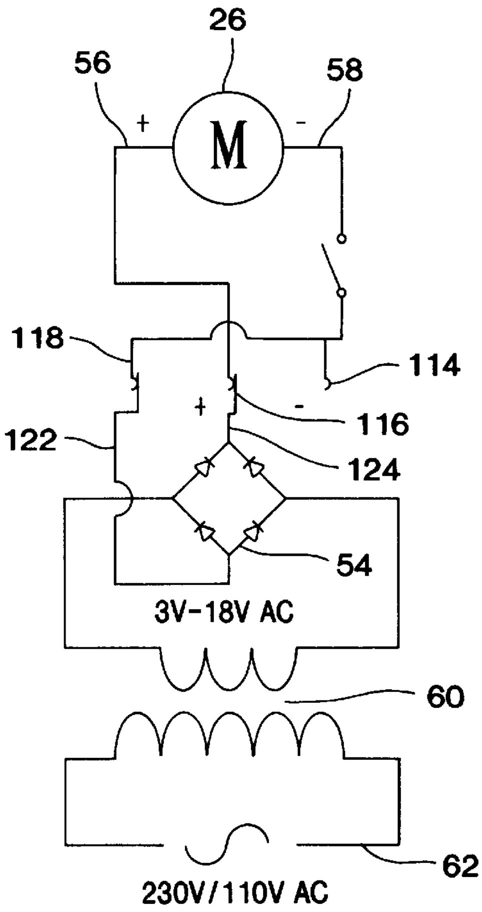
Figure 18A:
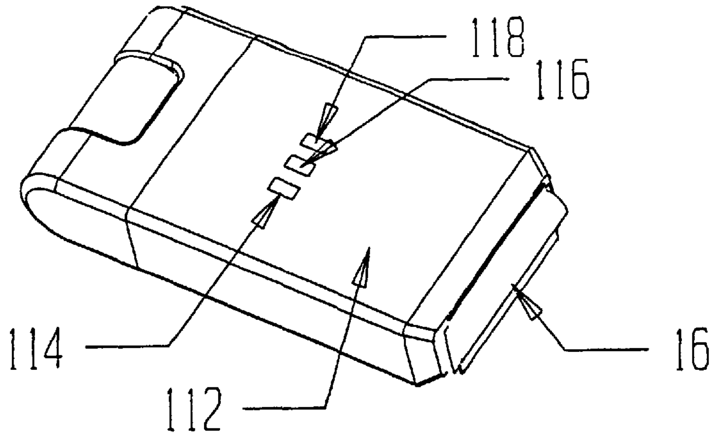
FIGS. 18A through 18C are various views of contacts externally exposed from the casing and terminals of the handle according to the fifth embodiment of the present invention.
Figure 18B:
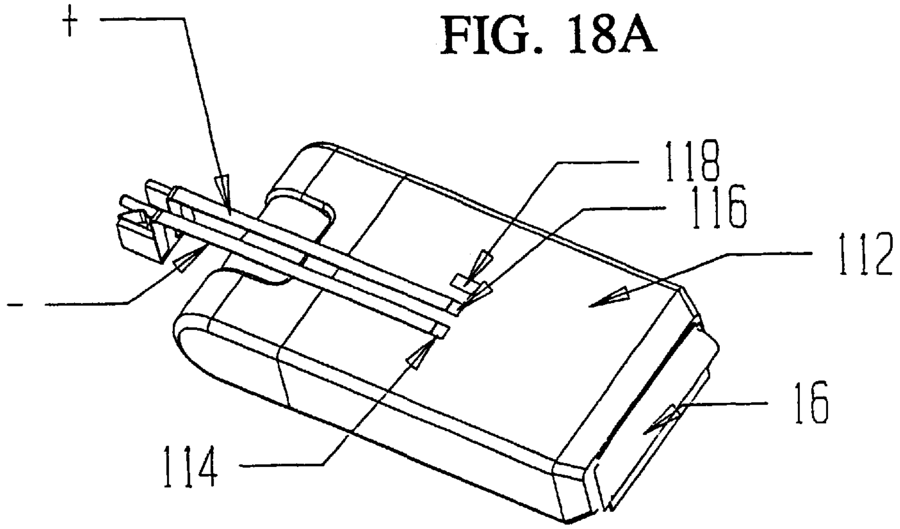
Figure 18C:
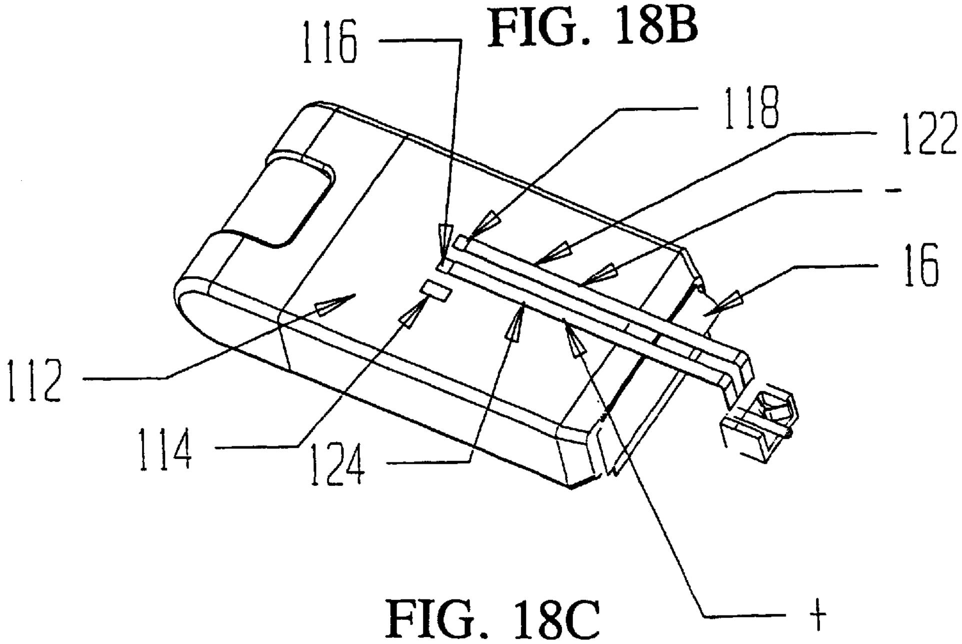

As shown in FIGS. 17A and 18B, when the handle 20 is attached at one end of the casing 112 to cover the epilating head 14, the terminal 124 contacts the center contact 116 and the terminal 122 contacts the outer contact 114. As shown in FIGS. 17B, 18C and 19B, when the handle 20 is attached to the other end of the casing 112 so as to cover the depilating head 16, the terminal 124 contacts the center contact 116 and the terminal 122 contacts the outer lead 118.

Figure 19A:
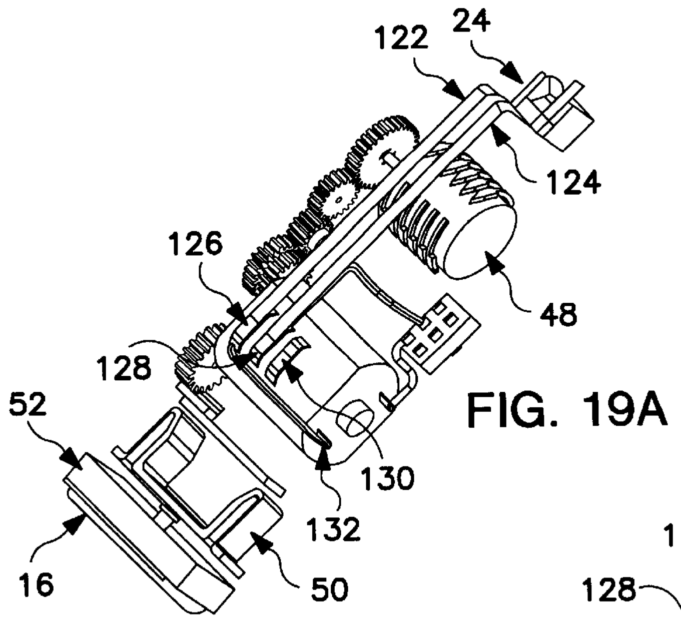
FIGS. 19A through 19C are various views of the internal mechanical configuration and internal electrical circuitry of the casing according to the fifth embodiment of the present invention.
Figure 19B:
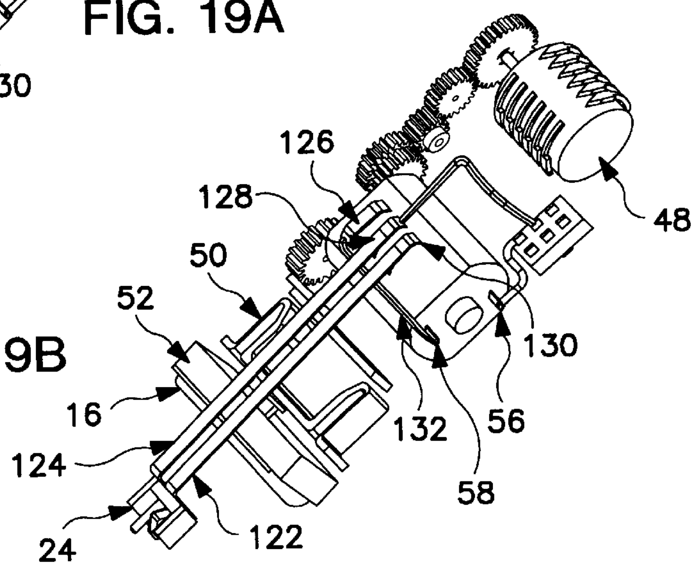
Figure 19C:
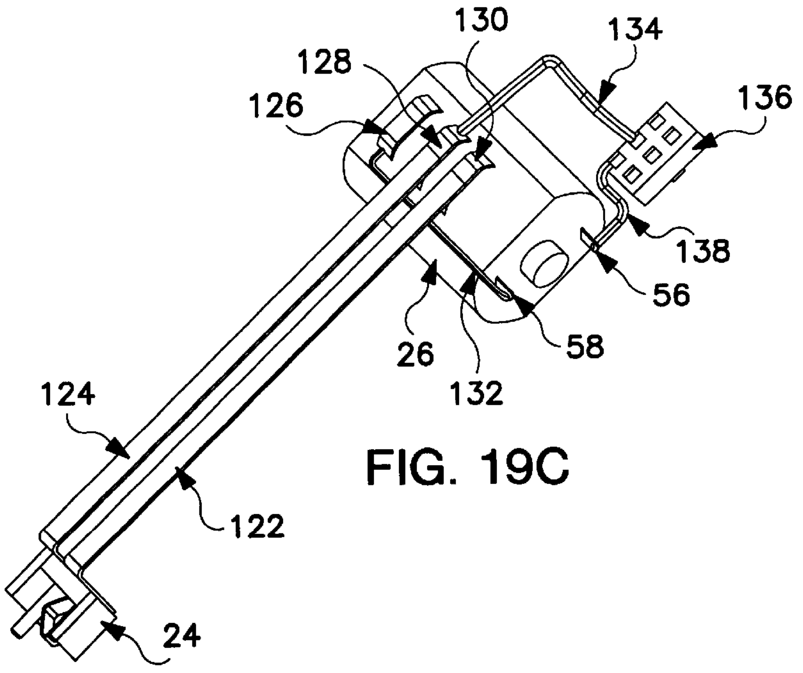

FIG. 19C shows a closeup of FIG. 19B, and shows a conductor 126 of the motor 26 having a minus polarity, a conductor 128 having a positive polarity, and a conductor 130 of the motor 26 having a negative polarity. A wire 132 connects the conductors 126, 130 to the negative terminal 58 of the motor 26. A wire 134 connects the conductor 128 with a switch 136. A wire 138 connects the switch 136 to the positive lead 56 of the motor.

Regardless of at which end of the casing 12 the handle 20 attaches, the terminal 124 contacts the positive conductor 128, and the terminal 122 contacts either of the negative conductors 126, 130.

Although FIGS. 19A through 19C show a mechanical configuration similar to that shown in FIGS. 7A and 7B, other mechanical configurations such as those shown in FIGS. 2A and 2B, and 6A and 6B may be used with the three-contact AC power systems.

Figure 20A:
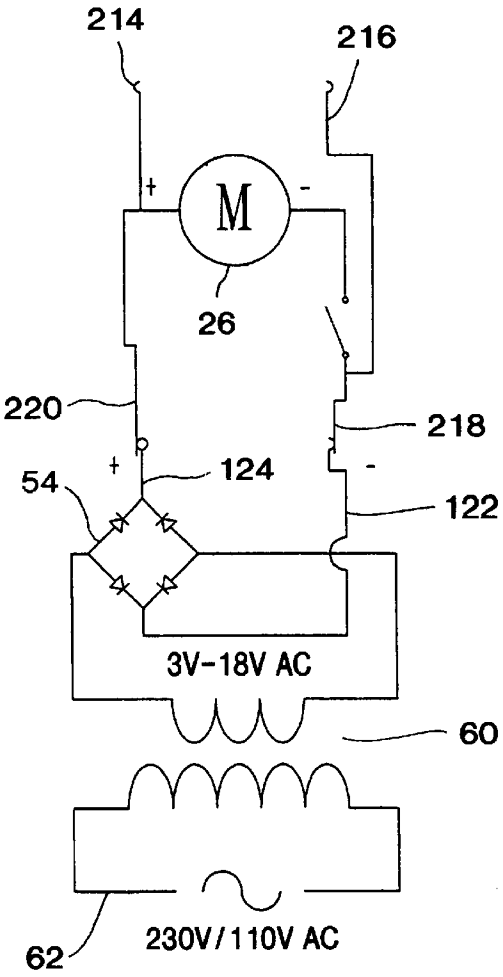
FIGS. 20A and 20B show the internal circuitry of a casing using a four-contact AC system according to a sixth embodiment of the present invention.
Figure 20B:
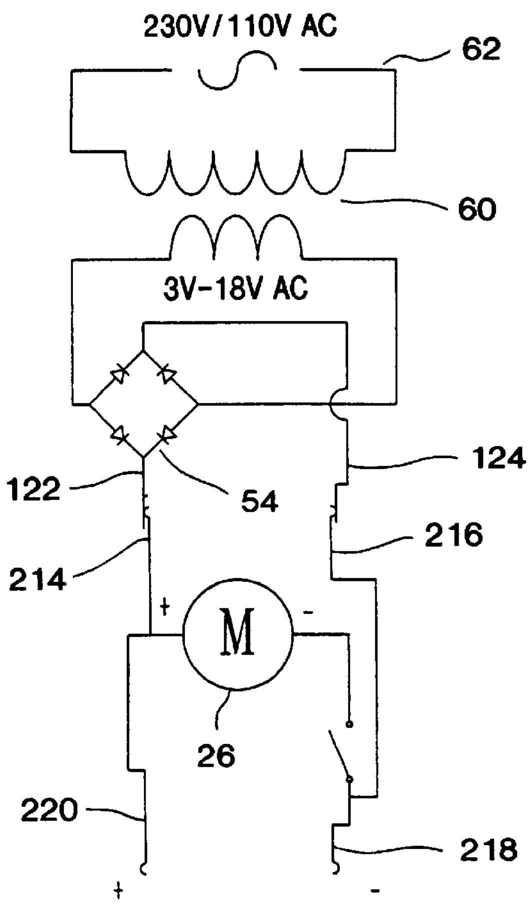
Figure 21A:
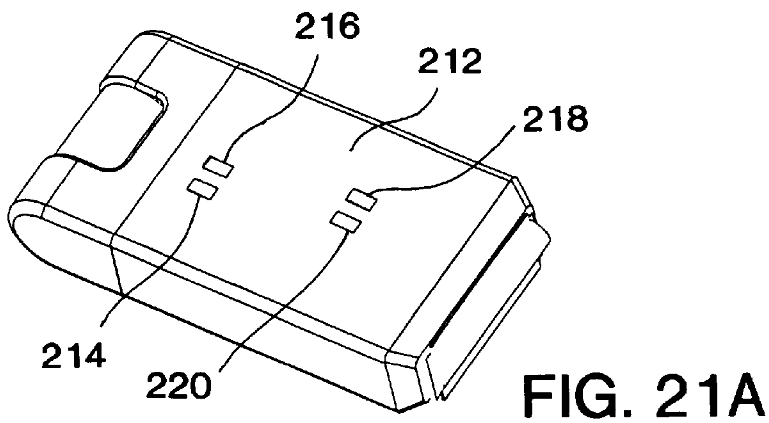
FIGS. 21A through 21C show various views of the contacts of the casing and terminals of the handle according to the sixth embodiment of the present invention.
Figure 21B:
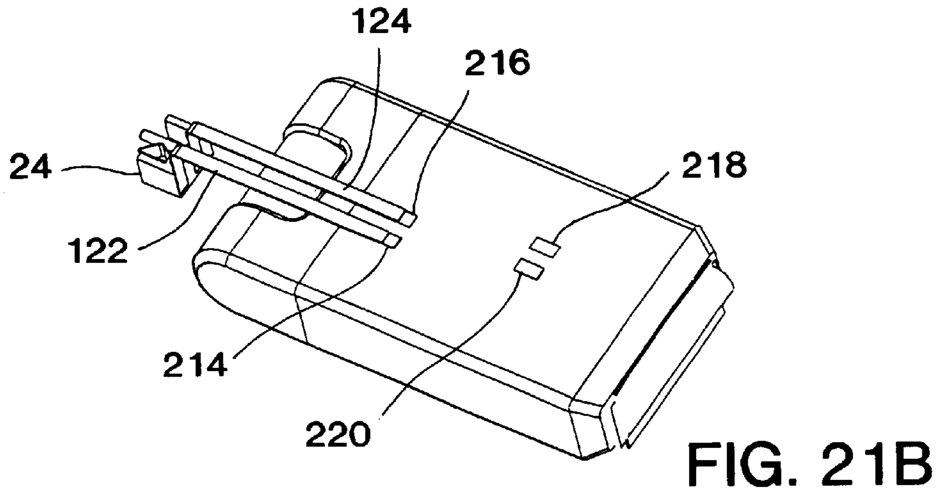
Figure 21C:
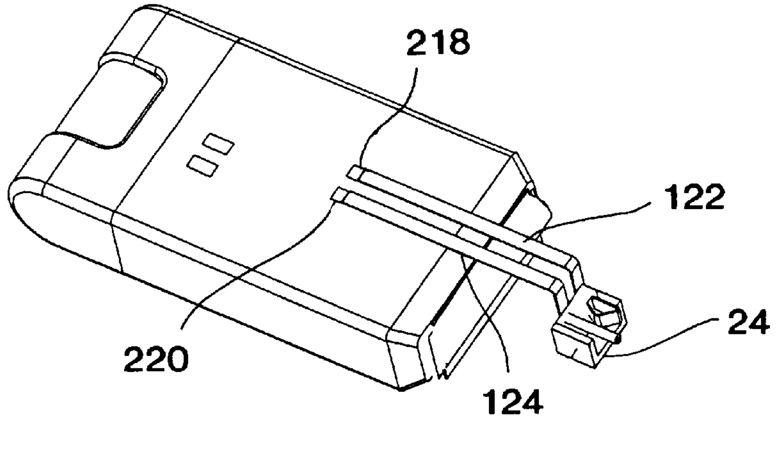

FIGS. 20A through 21C show a four-contact AC power electrical system according to a sixth embodiment of the present invention. The casing 212 as shown in FIGS. 21A through 21C differs from casings 12, 112 in that there are four contacts 214, 216, 218, 220 which are externally exposed from the casing 212. The terminals 122, 124 of the handle 20 contact either the contacts 214, 216 or contacts 218, 220, depending upon which end of the casing 212 at which the handle 20 attaches.

FIGS. 20A and 20B show that there are two separate contact systems which are combined within the casing 212. The rectifier 54 provides DC power from the terminals 122, 124 to the contacts 214, 216 or the contacts 218, 220. The rectifier 54 is in an outside adapter (not shown) external to the dual ended hair remover 10.

As one can see, there are numerous power electrical circuits which may drive the motor to operate the epilating head 14 and the depilating head 16. The three-contact or four-contact AC system according to the fifth and sixth embodiments may be used in any of the first through fourth embodiments. One of ordinary skill in the art would recognize that there may be other power electrical systems which would properly operate the motor 26.

Figure 22A:
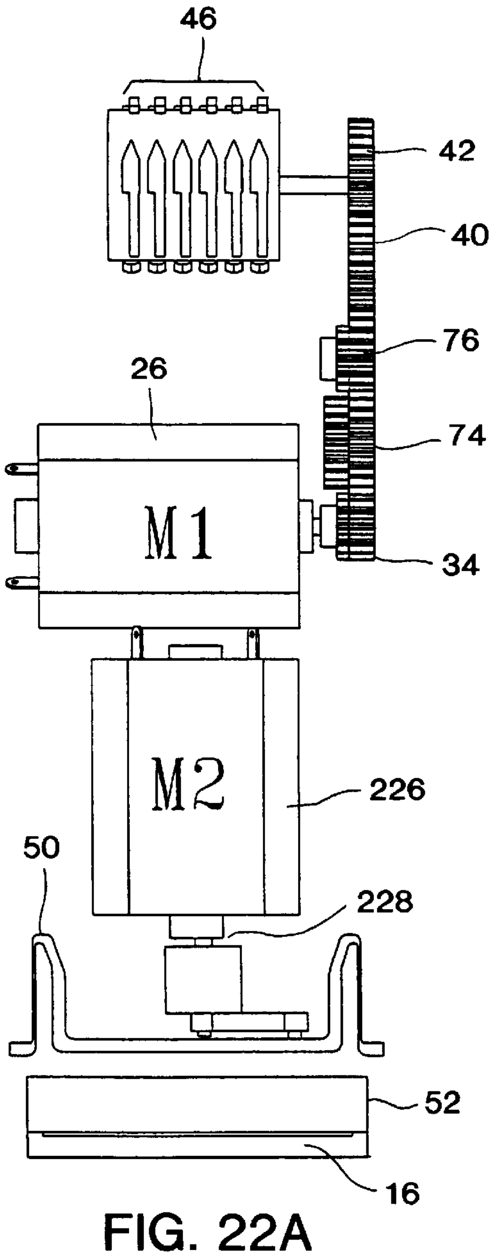
FIGS. 22A and 22B show a plan view and a perspective view of the internal mechanical configuration of a casing according to a seventh embodiment of the present invention.
Figure 22B:
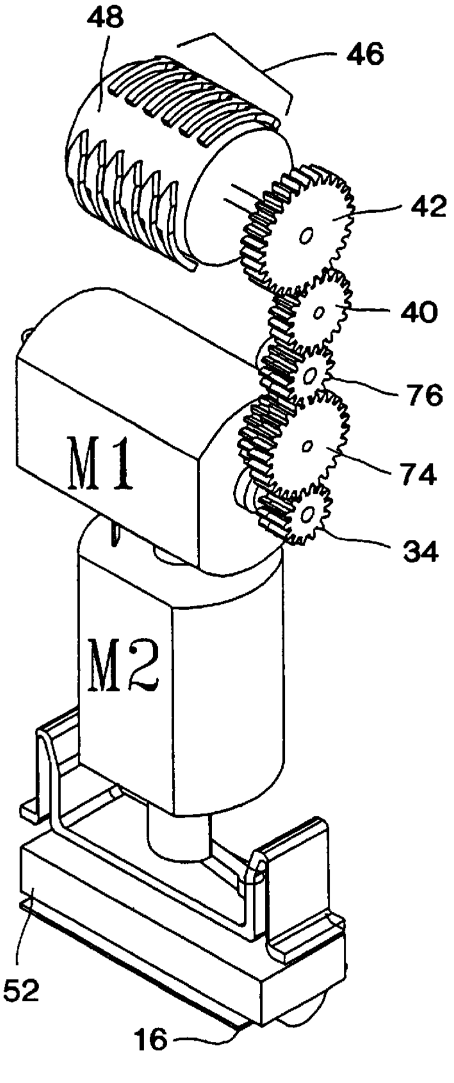

FIGS. 22A and 22B show a plan view and a perspective view of internal mechanical configuration for the casing 12 according to a seventh embodiment of the present invention. In the seventh embodiment, there is a second motor 226 in addition to the first motor 26. The configuration of the rotary gears 34, 74, 76, 40 and 42 in relation to powering the epilating head 14 is the same as that shown in FIGS. 6A and 6B, with the exception that the motor 26 is not movable within the casing 12. Thus, the motor 26 is used only to drive the epilating head 14, and not the depilating head 16.

The second motor 226 is positioned perpendicular to the motor 26, and has an axle 228 which is connected to the moving element 50 of the depilating head 16 so as to move the moving element 50 in a reciprocating motion relative to the fixed element 52, as in the other embodiments of the invention.

Figure 23A:
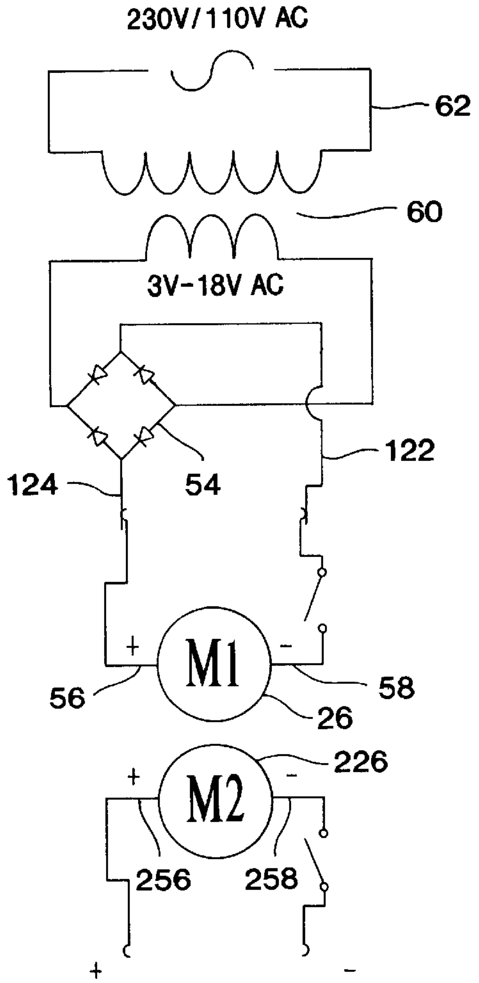
FIGS. 23A and 23B show the internal circuitry based upon whether a handle is attached to one end or the other end of the casing, respectively, according to the seventh embodiment of the present invention.
Figure 23B:
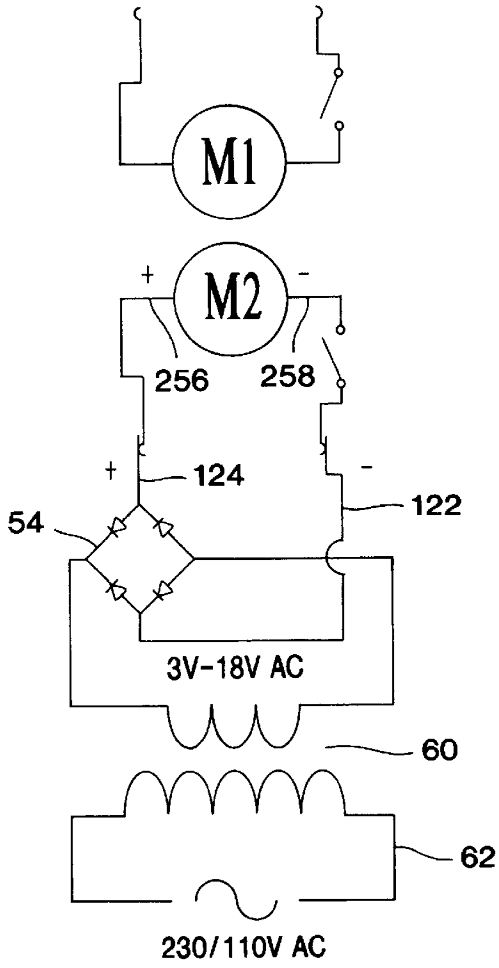
Figure 24:
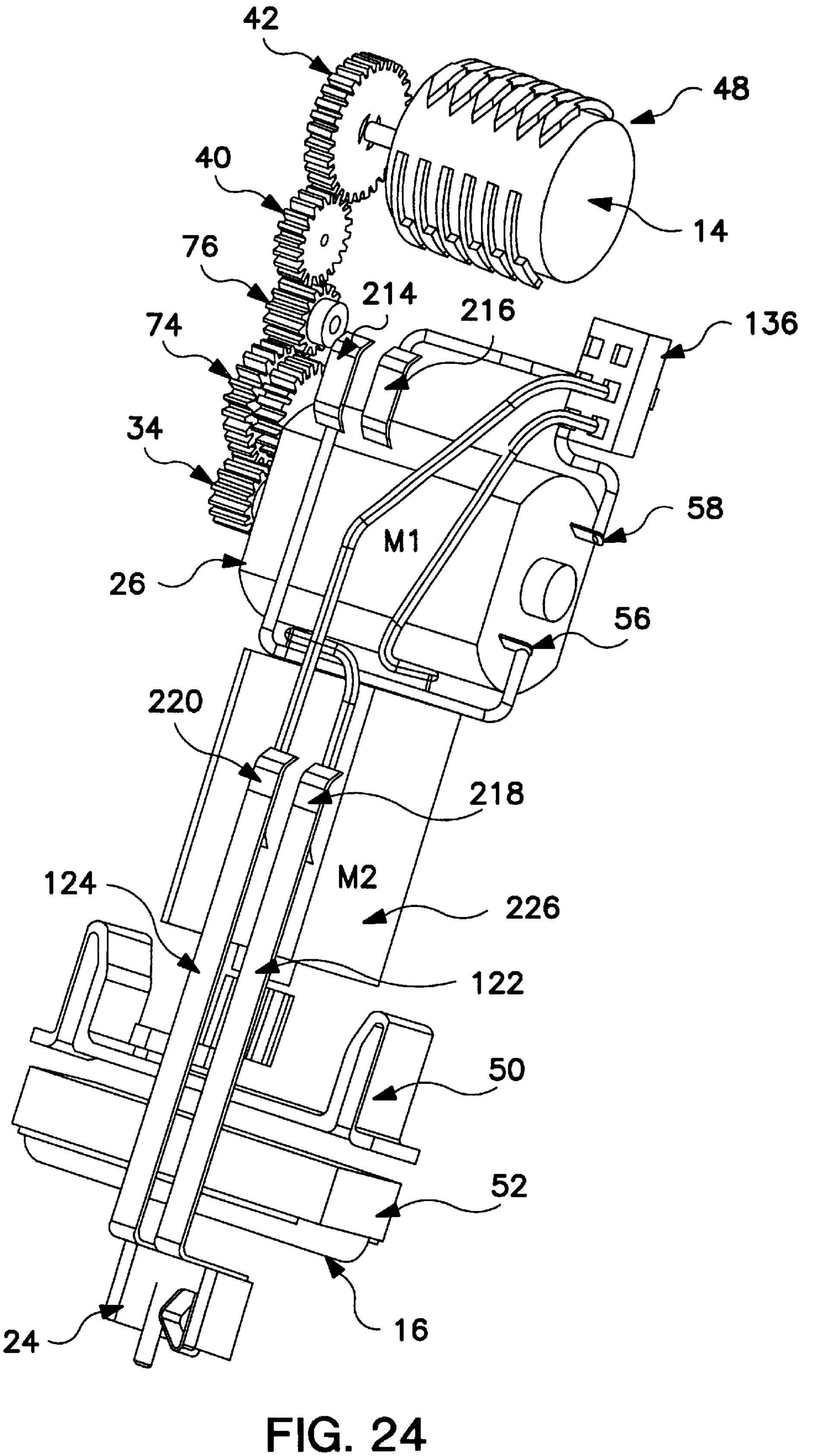
FIG. 24 is a perspective view of the internal mechanical configuration and internal electrical circuitry of the casing according to the seventh embodiment of the present invention.

FIGS. 23A and 23B are schematic electrical diagrams of the power electrical circuitry for driving the motors 26, 226. FIG. 24 shows the internal mechanical configuration of the casing 212 which has the contacts 214, 216, 218, 220 as in the sixth embodiment. The difference is that the contact 214 is connected to the negative pole 56 of the motor 26 and the contact 216 is connected to the switch 136. The contact 218 is connected to the negative pole 56 of the motor 226 and the contact 220 is connected to the switch 136. The positive and negative poles of the second motor 226 are 256, 258, respectively. The rectifier 54 is part of an outside adapter external to the dual ended hair remover 10.

Although a few preferred embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A dual ended hair remover to remove hairs from skin of a user, comprising:

a casing having first and second ends opposite each other;

an epilating head mounted on the first end, to pluck the hairs from the skin of the user; and a depilating head mounted on the second end, to cut the hairs from the skin of the user.

2. The dual ended hair remover as claimed in claim 1, further comprising:

a handle alternately mountable on the first and second ends of the casing, wherein when said handle is mounted on the first end, the handle covers the epilating head and enables driving of the depilating head, and when said handle is mounted on the second end, the handle covers the depilating head and enables driving of the epilating head.

3. The dual ended hair remover as claimed in claim 1, wherein the handle enables driving of the depilating head and the epilating head simultaneously.

4. The dual ended hair remover as claimed in claim 1, wherein the handle enables driving of only one of the depilating head and the epilating head at a given time.

5. The dual ended hair remover as claimed in claim 2, further comprising:

a motor having drive axles extending from opposite ends of the motor and poles, to drive the epilating and depilating heads;

drive gears connecting a first one of the drive axles to an axle of the epilating head;

contacts externally exposed from the handle and electrically connected to the poles of the motor;

wherein the second axle engages the depilating head, and the handle comprises terminals which engage with the contacts to provide power thereto when being mounted on the first and second ends of the casing.

6. The dual ended hair remover as claimed in claim 5, wherein:

the contacts comprise first and second contacts externally exposed at opposite sides of casing;

the terminals extend along opposite inner walls of the handle, to contact the contacts when mounted on the first and second ends of the casing.

7. The dual ended hair remover as claimed in claim 6, further comprising:

a regulator connected to the contacts, to convert AC power to DC power, and connected to the poles of the motor to provide the DC power to the motor; and the terminals provide the AC power to the contacts during contact between the terminals and the leads.

8. The dual ended hair remover as claimed in claim 5, wherein the drive gears comprise:

at least one first drive gear having an axis of rotation parallel to the axis of rotation of the motor, and one of the at least one first drive gear having teeth extending from a surface thereof in a direction parallel to the axis of rotation;

at least one second drive gear having an axis of rotation perpendicular to the axis of rotation of the motor, and one of the at least one second drive gear having teeth engaging the teeth of the one first drive gear;

wherein the axis of rotation of the motor is perpendicular to an axis of rotation of the epilating head.

9. The dual ended hair remover as claimed in claim 2, further comprising:

a motor having a drive axle extending from an end of the motor and poles, to drive the epilating and depilating heads;

drive gears connecting a first one of the drive axles to an axle of the epilating head;

a depilating axle extending from one of the drive gears to the depilating head; and contacts externally exposed from the handle and electrically connected to the poles of the motor;

wherein the handle comprises terminals which engage with the contacts to provide power thereto when being mounted on the first and second ends of the casing.

10. The dual ended hair remover as claimed in claim 9, wherein:

the contacts comprise first and second contacts externally exposed at opposite sides of casing;

the terminals extend along opposite inner walls of the handle, to contact the contacts when mounted on the first and second ends of the casing.

11. The dual ended hair remover as claimed in claim 10, further comprising:

a regulator connected to the contacts, to convert AC power to DC power, and connected to the poles of the motor to provide the DC power to the motor; and the terminals provide the AC power to the contacts during contact between the terminals and the leads.

12. The dual ended hair remover as claimed in claim 9, wherein the drive gears comprise:

at least one first drive gear having an axis of rotation parallel to the axis of rotation of the motor, and one of the at least one first drive gear having teeth extending from a surface thereof in a direction parallel to the axis of rotation;

at least one second drive gear having an axis of rotation perpendicular to the axis of rotation of the motor, and one of the at least one second drive gear having teeth engaging the teeth of the one first drive gear;

wherein depilating axle is coaxial with the at least one first drive gear, and the axis of rotation of the motor is perpendicular to an axis of rotation of the epilating head.

13. The dual ended hair remover as claimed in claim 2, further comprising:

a motor having a drive axle extending from an end of the motor and poles, to drive the epilating and depilating heads, the motor movable between a first position in response to the handle being mounted on the end of the casing covering the epilating head and a second position in response to the handle being mounted on the other end of the casing covering the depilating head;

an axle drive gear mounted on the drive axle of the motor;

first drive gears connected to an axle of the epilating head, engaging the axle drive gear when the motor is at the second position and disengaging the axle drive gear when the motor is at the first position;

second drive gears connected to the depilating head, engaging the axle drive gear when the motor is at the first position and disengaging the axle drive gear when the motor is at the second position; and contacts externally exposed from the handle and electrically connected to the poles of the motor;

wherein the handle comprises terminals which engage with the contacts to provide power thereto when being mounted on the first and second ends of the casing.

14. The dual ended hair remover as claimed in claim 13, wherein:

the contacts comprise first and second contacts externally exposed at opposite sides of casing;

the terminals extend along opposite inner walls of the handle, to contact the contacts when mounted on the first and second ends of the casing.

15. The dual ended hair remover as claimed in claim 8, further comprising:

a regulator connected to the contacts, to convert AC power to DC power, and connected to the poles of the motor to provide the DC power to the motor; and the terminals provide the AC power to the contacts during contact between the terminals and the leads.

16. The dual ended hair remover as claimed in claim 2, further comprising:

a motor having a drive axle extending from an end of the motor and poles, to drive the epilating and depilating heads, the motor having an axle drive gear connected to and coaxial with the drive axle;

at least one first drive gear for driving an axle of the epilating head;

at least one second drive gear for driving the depilating head;

a coupling unit to alternately connect the axle drive gear with the at least one first drive gear and the axle drive gear with the at least one second drive gear, based upon which end of the casing the handle is mounted;

contacts externally exposed from the handle and electrically connected to the poles of the motor;

wherein the handle comprises terminals which engage with the contacts to provide power thereto when being mounted on the first and second ends of the casing.

17. The dual ended hair remover as claimed in claim 16, wherein:

the contacts comprise first and second contacts externally exposed at opposite sides of casing;

the terminals extend along opposite inner walls of the handle, to contact the contacts when mounted on the first and second ends of the casing.

18. The dual ended hair remover as claimed in claim 17, further comprising:

a regulator connected to the contacts, to convert AC power to DC power, and connected to the poles of the motor to provide the DC power to the motor; and the terminals provide the AC power to the contacts during contact between the terminals and the leads.

19. The dual ended hair remover as claimed in claim 16, wherein the drive gears comprise:

at least one first drive gear having an axis of rotation parallel to the axis of rotation of the motor, and one of the at least one first drive gear having teeth extending from a surface thereof in a direction parallel to the axis of rotation;

at least one second drive gear having an axis of rotation perpendicular to the axis of rotation of the motor, and one of the at least one second drive gear having teeth engaging the teeth of the one first drive gear;

wherein the axis of rotation of the motor is perpendicular to an axis of rotation of the epilating head.

20. The dual ended hair remover as claimed in claim 16, wherein:

the coupling unit comprises:

a rotary gear engaging the axle drive gear, and having a thickened region with first slots extending from a surface of the rotary gear, a drive gear having teeth and protrusions extended from a surface thereof, wherein the teeth engage one of the at least one first gears, the drive gear coaxial with the rotary gear, a depilating axle connected to the depilating head, having a spline with second slots coaxial with the depilating axle, and a coupler with recesses, and protrusions which extend along a height of the coupler;

wherein the coupler moves between a first position such that the protrusions engage the first slots and do not engage the second slots, and the recesses engage corresponding ones of the protrusions so that rotation of the rotary gear causes rotation of the thickened region, the coupler, the first drive gears, to drive the epilating head, and a second position such that the protrusions engage both the first and second slots and the recesses disengage from the corresponding protrusions so that the rotation of the rotary gear causes rotation of the thickened region, the coupler, the spline, and the depilating axle, to drive the depilating head.

21. The dual ended hair remover as claimed in claim 20, further comprising:

an attachment mounted in the casing and attached to the coupler, wherein the selective mounting of the handle on the ends of the casing moves the attachment so that the coupler moves between the first and second positions.

22. The dual ended hair remover as claimed in claim 21, wherein the handle and the attachment move the coupler to the first position when the handle covers the depilating head, and move the coupler to the second position when the handle covers the epilating head.

23. The dual ended hair remover as claimed in claim 20, further comprising:

an attachment mounted in the casing and attached to the coupler; and a spring to bias the attachment so that coupler is at one of the first and second positions;

wherein the mounting of the handle on one of the ends of the casing causes the attachment to move the coupler to the other one of the first and second positions against the bias of the spring.

24. The dual ended hair remover as claimed in claim 2, further comprising:

a motor having first and second poles of a first bias and a third poles of a second bias, to drive the epilating and depilating heads;

drive gears connecting the motor to an axle of the epilating head; and first through third contacts externally exposed from the handle and electrically connected to the first through third poles of the motor;

wherein the handle comprises first and second terminals which engage with the first and third contacts to provide power thereto when being mounted on the first end of the casing, and which engage with the second and third contacts to provide the power thereto when being mounted on the second end of the casing.

25. The dual ended hair remover as claimed in claim 24, wherein the first and second terminals extend along an inner side walls of the handle, to contact the first and third, or second and third contacts, when mounted on the first and second ends of the casing, respectively.

26. The dual ended hair remover as claimed in claim 24, further comprising:

a regulator having opposite ends connected to the first and third contacts or the second and third contacts, to convert AC power to DC power based upon at which end of the casing the handle is mounted, wherein the first and third contacts or the second and third contacts are connected to the poles of first and second bias of the motor, respectively, to provide the DC power to the motor; and the first and second terminals provide the AC power to the first and third contacts or the second and third contacts during contact between the first and second terminals and the first and third contacts or the second and third contacts, respectively.

27. The dual ended hair remover as claimed in claim 12, further comprising:

a motor having first and second poles of a first bias and a third pole of a second bias, to drive the epilating and depilating heads;

drive gears connecting the motor to an axle of the epilating head;

first through third contacts externally exposed from the handle and electrically connected to the first through third poles of the motor;

the handle comprising first and second terminals which engage with the first and third contacts to provide power thereto when being mounted on the first end of the casing, and which engage with the second and third contacts to provide the power thereto when being mounted on the second end of the casing; and a regulator having opposite ends connected to the first and third contacts or the second and third contacts, to convert AC power to DC power based upon at which end of the casing the handle is mounted, wherein the first and third contacts or the second and third contacts are connected to the poles of first and second bias of the motor, respectively, to provide the DC power to the motor;

wherein the first and second terminals provide the AC power to the first and third contacts or the second and third contacts during contact between the first and second terminals and the first and third contacts or the second and third contacts, respectively.

28. The dual ended hair remover as claimed in claim 16, further comprising:

a motor having first and second poles of a first bias and a third pole of a second bias, to drive the epilating and depilating heads;

drive gears connecting the motor to an axle of the epilating head;

first through third contacts externally exposed from the handle and electrically connected to the first through third poles of the motor;

the handle comprising first and second terminals which engage with the first and third contacts to provide power thereto when being mounted on the first end of the casing, and which engage with the second and third contacts to provide the power thereto when being mounted on the second end of the casing; and a regulator having opposite ends connected to the first and third contacts or the second and third contacts, to convert AC power to DC power based upon at which end of the casing the handle is mounted, wherein the first and third contacts or the second and third contacts are connected to the poles of first and second bias of the motor, respectively, to provide the DC power to the motor;

wherein the first and second terminals provide the AC power to the first and third contacts or the second and third contacts during contact between the first and second terminals and the first and third contacts or the second and third contacts, respectively.

29. The dual ended hair remover as claimed in claim 20, further comprising:

a motor having first and second poles of a first bias and a third pole of a second bias, to drive the epilating and depilating heads;

drive gears connecting the motor to an axle of the epilating head;

first through third contacts externally exposed from the handle and electrically connected to the first through third poles of the motor;

the handle comprising first and second terminals which engage with the first and third contacts to provide power thereto when being mounted on the first end of the casing, and which engage with the second and third contacts to provide the power thereto when being mounted on the second end of the casing; and a regulator having opposite ends connected to the first and third contacts or the second and third contacts, to convert AC power to DC power based upon at which end of the casing the handle is mounted, wherein the first and third contacts or the second and third contacts are connected to the poles of first and second bias of the motor, respectively, to provide the DC power to the motor;

wherein the first and second terminals provide the AC power to the first and third contacts or the second and third contacts during contact between the first and second terminals and the first and third contacts or the second and third contacts, respectively.

30. The dual ended hair remover as claimed in claim 2, further comprising:

a motor having first and second poles of opposite bias, to drive the epilating and depilating heads;

drive gears connecting the motor to an axle of the epilating head; and first through fourth contacts externally exposed from the handle, wherein the first and third contacts are electrically connected to the first pole of the motor, and the second and fourth contacts are electrically connected to the second pole of the motor;

wherein the handle comprises first and second terminals which engage with the first and third contacts to provide power thereto when being mounted on the first end of the casing, and which engage with the second and fourth contacts to provide the power thereto when being mounted on the second end of the casing.

31. The dual ended hair remover as claimed in claim 30, wherein the first and second terminals extend along an inner side walls of the handle, to contact the first and third, or second and fourth contacts, when mounted on the first and second ends of the casing, respectively.

32. The dual ended hair remover as claimed in claim 31, further comprising:

a regulator having opposite ends connected to the first and third contacts or the second and third contacts, to convert AC power to DC power based upon at which end of the casing the handle is mounted, wherein the first and third contacts or the second and fourth contacts are connected to the poles of first and second bias of the motor, respectively, to provide the DC power to the motor; and the first and second terminals provide the AC power to the first and third contacts or the second and fourth contacts during contact between the first and second terminals and the first and third contacts or the second and fourth contacts, respectively.

33. The dual ended hair remover as claimed in claim 12, further comprising:

a motor having first and second poles of opposite second bias, to drive the epilating and depilating heads;

drive gears connecting the motor to an axle of the epilating head;

first through third contacts externally exposed from the handle and electrically connected to the first through third poles of the motor;

the handle comprising first and second terminals which engage with the first and third contacts to provide power thereto when being mounted on the first end of the casing, and which engage with the second and third contacts to provide the power thereto when being mounted on the second end of the casing; and a regulator having opposite ends connected to the first and third contacts or the second and fourth contacts, to convert AC power to DC power based upon at which end of the casing the handle is mounted, wherein the first and third contacts or the second and fourth contacts are connected to the poles of first and second bias of the motor, respectively, to provide the DC power to the motor;

wherein the first and second terminals provide the AC power to the first and third contacts or the second and fourth contacts during contact between the first and second terminals and the first and third contacts or the second and fourth contacts, respectively.

34. The dual ended hair remover as claimed in claim 16, further comprising:

a motor having first and second poles of opposite second bias, to drive the epilating and depilating heads;

drive gears connecting the motor to an axle of the epilating head;

first through third contacts externally exposed from the handle and electrically connected to the first through third poles of the motor;

the handle comprising first and second terminals which engage with the first and third contacts to provide power thereto when being mounted on the first end of the casing, and which engage with the second and third contacts to provide the power thereto when being mounted on the second end of the casing; and a regulator having opposite ends connected to the first and third contacts or the second and fourth contacts, to convert AC power to DC power based upon at which end of the casing the handle is mounted, wherein the first and third contacts or the second and fourth contacts are connected to the poles of first and second bias of the motor, respectively, to provide the DC power to the motor;

wherein the first and second terminals provide the AC power to the first and third contacts or the second and fourth contacts during contact between the first and second terminals and the first and third contacts or the second and fourth contacts, respectively.

35. The dual ended hair remover as claimed in claim 20, further comprising:

a motor having first and second poles of opposite second bias, to drive the epilating and depilating heads;

drive gears connecting the motor to an axle of the epilating head;

first through third contacts externally exposed from the handle and electrically connected to the first through third poles of the motor;

the handle comprising first and second terminals which engage with the first and third contacts to provide power thereto when being mounted on the first end of the casing, and which engage with the second and third contacts to provide the power thereto when being mounted on the second end of the casing; and a regulator having opposite ends connected to the first and third contacts or the second and fourth contacts, to convert AC power to DC power based upon at which end of the casing the handle is mounted, wherein the first and third contacts or the second and fourth contacts are connected to the poles of first and second bias of the motor, respectively, to provide the DC power to the motor;

wherein the first and second terminals provide the AC power to the first and third contacts or the second and fourth contacts during contact between the first and second terminals and the first and third contacts or the second and fourth contacts, respectively.

36. The dual ended hair remover as claimed in claim 2, further comprising:

a first motor having first and second poles of opposite bias, to drive the epilating head;

a second motor having third and fourth poles of opposite bias, to drive the depilating head;

drive gears connecting the motor to an axle of the epilating head; and first through fourth contacts externally exposed from the handle, wherein the first and second contacts are electrically connected to the first and second poles of the first motor, respectively, and the third and fourth contacts are electrically connected to the third and fourth poles of the second motor;

wherein the handle comprises first and second terminals which engage with the first and second contacts to provide power thereto when being mounted on the first end of the casing, and which engage with the third and fourth contacts to provide the power thereto when being mounted on the second end of the casing.

37. The dual ended hair remover as claimed in claim 36, wherein the first and second terminals extend along an inner side walls of the handle, to contact the first and second, or third and fourth contacts, when mounted on the first and second ends of the casing, respectively.

38. The dual ended hair remover as claimed in claim 36, further comprising:

a regulator having opposite ends connected to the first and second contacts or the third and fourth contacts, to convert AC power to DC power based upon at which end of the casing the handle is mounted, wherein the first and second contacts or the third and fourth contacts are connected to the first and second poles of the first motor or the third and fourth poles of the second motor, respectively, to provide the DC power to the motor; and the first and second terminals provide the AC power to the first and second contacts or the third and fourth contacts during contact between the first and second terminals and the first and second contacts or the third and fourth contacts, respectively.

39. A dual ended hair remover to remove hairs from skin of a user, comprising:

a casing having first and second ends opposite each other;

an epilating head mounted on the casing, to pluck the hairs from the skin of the user;

a depilating head mounted on the casing, to cut the hairs from the skin of the user; and a handle to alternately cover the epilating head and enable driving of the depilating head, and cover the depilating head and enable driving of the epilating head.

40. The dual ended hair remover as claimed in claim 39, wherein the epilating head is mounted at one end of the casing and the depilating head is mounted at the other end of the casing.

41. A dual ended hair remover to remove hairs from skin of a user, comprising:

a casing having first and second ends opposite each other;

an epilating head mounted on the casing, to pluck the hairs from the skin of the user;

a depilating head mounted on the casing, to cut the hairs from the skin of the user; and a handle to alternately cover the epilating head and enable driving of the depilating head without enabling driving of the epilating head, and cover the depilating head and enable driving of the epilating head without enabling driving of the depilating head.

* * * * *